US008147834B2

(12) United States Patent
Wu

(10) Patent No.: US 8,147,834 B2
(45) Date of Patent: Apr. 3, 2012

(54) ANTI-TGF-BETA RECEPTOR II ANTIBODIES

(75) Inventor: Yan Wu, Flemington, NJ (US)

(73) Assignee: ImClone LLC, New York, NY (US)

( * ) Notice: Subject to any disclaimer, the term of this patent is extended or adjusted under 35 U.S.C. 154(b) by 306 days.

(21) Appl. No.: 12/608,034

(22) Filed: Oct. 29, 2009

(65) Prior Publication Data

US 2010/0119516 A1    May 13, 2010

Related U.S. Application Data

(60) Provisional application No. 61/198,697, filed on Nov. 7, 2008, provisional application No. 61/170,369, filed on Apr. 17, 2009.

(51) Int. Cl.
*A61K 39/395* (2006.01)
*C07K 16/18* (2006.01)

(52) U.S. Cl. ............ 424/133.1; 424/139.1; 530/387.9

(58) Field of Classification Search ............ 424/133.1, 424/139.1; 530/387.9
See application file for complete search history.

(56) References Cited

U.S. PATENT DOCUMENTS 5,565,332 A  10/1996  Hoogenboom
6,201,108 B1  3/2001  Lin

FOREIGN PATENT DOCUMENTS

EP  1992360  11/2008
JP  2004121001  4/2004

OTHER PUBLICATIONS

Brown, et al., Developmental Biology 174:248-257 (1996).
Carroll, et al., Jun. 2009, AACR, Denver, CO, Anti-TGF beta receptor II antibody abrogates FoxP3+/TGF β RII + Treg cells and enhances antitumor immunity against tumor growth and metastasis.
Fukasawa, et al., Kidney International 65:63-74 (2004).
Harlow & Lane, ed., Antibodies: A Laboratory Manual, Cold Spring Harbor, pp. 211-213 (1998).
Honeychurch, et al., Cancer Res. 65(16):7493-7501 (2005).
Jones, et al., Nature 321:522 (1986).
Kasuga, et al., Kidney International 60:1745-1755 (2001).
Co, et al., Proc. Natl. Acad. Sci. USA 88:2869-2873 (1991) (Queen reference).
Remington, The Science and Practice of Pharmacy, 19th Edition, Gennaro, Ed., Mack Publishing Co., Easton, PA 1995.
Riechmann, et al., Nature 332:323-327 (1988).
Tessler, J. Biol. Chem. 269(17):12456-12461 (1994).
Verhoeyen, et al., Science 239:1534-1536 (1988).
Wu, et al., J. Mol. Biol. 294(1):151-162 (1999).

*Primary Examiner* — Lynn Bristol
(74) *Attorney, Agent, or Firm* — Averie K. Hason

(57) ABSTRACT

The present invention is directed to antibodies against human transforming growth factor beta receptor II (TGFβRII), pharmaceutical compositions comprising antibodies and methods of using the antibodies, alone or in combination, for example, for treating cancer and fibrosis.

5 Claims, No Drawings

SEQUENCE LISTING

```
<160> NUMBER OF SEQ ID NOS: 42

<210> SEQ ID NO 1
<211> LENGTH: 9
<212> TYPE: PRT
<213> ORGANISM: Homo sapiens

<400> SEQUENCE: 1

Gly Gly Ser Ile Ser Asn Ser Tyr Phe
1               5

<210> SEQ ID NO 2
<211> LENGTH: 16
<212> TYPE: PRT
<213> ORGANISM: Homo sapiens

<400> SEQUENCE: 2

Ser Phe Tyr Tyr Gly Glu Lys Thr Tyr Tyr Asn Pro Ser Leu Lys Ser
1               5                   10                  15

<210> SEQ ID NO 3
<211> LENGTH: 11
<212> TYPE: PRT
<213> ORGANISM: Homo sapiens

<400> SEQUENCE: 3

Gly Pro Thr Met Ile Arg Gly Val Ile Asp Ser
1               5                   10

<210> SEQ ID NO 4
<211> LENGTH: 214
<212> TYPE: PRT
<213> ORGANISM: Artificial
<220> FEATURE:
<223> OTHER INFORMATION: Synthetic

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 711
<212> TYPE: DNA
<213> ORGANISM: Artificial
<220> FEATURE:
<223> OTHER INFORMATION: Synthetic

<400> SEQUENCE: 5
gccgccacca tgggatggtc atgtatcatc cttttctgg tagcaactgc aactggagta       60
cattcagaaa ttgtgttgac acagtctcca gccaccctgt ctttgtctcc aggggaaaga     120
gccaccctct cctgcagggc cagtcagagt gttcgcagct acttagcctg gtaccaacag     180
aaacctggcc aggctcccag gctcctcatc tatgatgcat ccaacagggc cactggcatc     240
ccagccaggt tcagtggcag tgggtctggg acagacttca ctctcaccat cagcagccta     300
gagcctgaag attttgcagt ttattactgt cagcagcgta gcaactggcc tccgacgttc     360
ggccaaggga ccaaggtgga aatcaaacga actgtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggaaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g             711

<210> SEQ ID NO 6
<211> LENGTH: 451
<212> TYPE: PRT
<213> ORGANISM: Artificial
<220> FEATURE:
<223> OTHER INFORMATION: Synthetic

<400> SEQUENCE: 6

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ser Trp Gly Trp Ile Arg Gln Pro Pro Gly Lys Gly Leu Glu
        35                  40                  45

Trp Ile Gly Ser Phe Tyr Tyr Ser Gly Ile Thr Tyr Tyr Ser Pro Ser
    50                  55                  60

Leu Lys Ser Arg Ile Ile Ile Ser Glu Asp Thr Ser Lys Asn Gln Phe
65              70                  75                  80

Ser Leu Lys Leu Ser Ser Val Thr Ala Ala Asp Thr Ala Val Tyr Tyr
                85                  90                  95

Cys Ala Ser Gly Phe Thr Met Ile Arg Gly Ala Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
                420                 425                 430
His Glu Ala Leu His Asn His Tyr Thr Gln Lys Ser Leu Ser Leu Ser
            435                 440                 445

Pro Gly Lys
    450

<210> SEQ ID NO 7
<211> LENGTH: 9
<212> TYPE: PRT
<213> ORGANISM: Homo sapiens

<400> SEQUENCE: 7

Gly Gly Ser Ile Ser Ser Ser Ser Tyr
1               5

<210> SEQ ID NO 8
<211> LENGTH: 16
<212> TYPE: PRT
<213> ORGANISM: Homo sapiens

<400> SEQUENCE: 8

Ser Phe Tyr Tyr Ser Gly Ile Thr Tyr Tyr Ser Pro Ser Leu Lys Ser
1               5                   10                  15

<210> SEQ ID NO 9
<211> LENGTH: 11
<212> TYPE: PRT
<213> ORGANISM: Homo sapiens

<400> SEQUENCE: 9

Gly Phe Thr Met Ile Arg Gly Ala Leu Asp Tyr
1               5                   10

<210> SEQ ID NO 10
<211> LENGTH: 11
<212> TYPE: PRT
<213> ORGANISM: Homo sapiens

<400> SEQUENCE: 10

Arg Ala Ser Gln Ser Val Arg Ser Tyr Leu Ala
1               5                   10

<210> SEQ ID NO 11
<211> LENGTH: 7
<212> TYPE: PRT
<213> ORGANISM: Homo sapiens

<400> SEQUENCE: 11

Asp Ala Ser Asn Arg Ala Thr
1               5

<210> SEQ ID NO 12
<211> LENGTH: 9
<212> TYPE: PRT
<213> ORGANISM: Homo sapiens

<400> SEQUENCE: 12

Gln Gln Arg Ser Asn Trp Pro Pro Thr
1               5

<210> SEQ ID NO 13
<211> LENGTH: 1413
<212> TYPE: DNA
<213> ORGANISM: Artificial
<220> FEATURE:
```

<223> OTHER INFORMATION: Synthetic

<400> SEQUENCE: 13

```
atgggatggt catgtatcat ccttttcta gtagcaactg caactggagt acattcacag      60
ctacagctgc aggagtcggg cccaggactg gtgaagcctt cggagaccct atccctcacc    120
tgcactgtct ctggtggctc catcagcagt agtagttact cctggggctg gatccgccag    180
cccccaggga agggcctgga gtggattggg agtttctatt acagtgggat cacctactac    240
agcccgtccc tcaagagtcg aattatcata tccgaagaca cgtccaagaa ccagttctcc    300
ctgaagctga gttctgtgac cgccgcagac acggctgtgt attactgtgc gagcgggttt    360
actatgattc ggggagccct tgactactgg ggccagggaa ccctggtcac cgtctcctca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagag agttgagccc    720
aaatcttgtg acaaaactca cacatgccca ccgtgcccag cacctgaact cctgggggga    780
ccgtcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tatgtggacg gcgtggaggt gcataatgcc aagacaaagc cgcgggagga gcagtacaac    960
agcacgtacc gtgtggtcag cgtcctcacc gtcctgcacc aagactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggaggag   1140
atgaccaaga accaagtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctat tccaagctca ccgtggacaa gagcaggtgg   1320
cagcagggga acgtcttctc atgctccgtg atgcatgagg ctctgcacaa ccactacacg   1380
cagaagagcc tctccctgtc tccgggcaaa tga                                1413
```

<210> SEQ ID NO 14
<211> LENGTH: 214
<212> TYPE: PRT
<213> ORGANISM: Artificial
<220> FEATURE:
<223> OTHER INFORMATION: Synthetic

<400> SEQUENCE: 14

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 15
<211> LENGTH: 711
<212> TYPE: DNA
<213> ORGANISM: Artificial
<220> FEATURE:
<223> OTHER INFORMATION: Synthetic

<400> SEQUENCE: 15
gccgccacca tgggatggtc atgtatcatc cttttctgg tagcaactgc aactggagta      60
cattcagaaa ttgtgttgac acagtctcca gccaccctgt ctttgtctcc aggggaaaga   120
gccaccctct cctgcagggc cagtcagagt gttagaagtt tcttagcctg gtaccaacag   180
aaacctggcc aggctcccag gctcctcatc tatgatgcat ccaacagggc cactggcatc   240
ccagccaggt tcagtggcag tgggtctggg acagacttca ctctcaccat cagcagccta   300
gagcctgaag attttgcagt ttattactgt cagcagcgta gcaactggcc tccgacgttc   360
ggccaaggga ccaaggtgga aatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggaaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta g            711
```

```
<210> SEQ ID NO 16
<211> LENGTH: 11
<212> TYPE: PRT
<213> ORGANISM: Homo sapiens

<400> SEQUENCE: 16

Arg Ala Ser Gln Ser Val Arg Ser Phe Leu Ala
1               5                   10
```

```
<210> SEQ ID NO 17
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa at position 6 = N or S
```

```
<220> FEATURE:
<221> NAME/KEY: MISC_FEATURE
<222> LOCATION: (8)..(8)
<223> OTHER INFORMATION: Xaa at position 8 = Y or S
<220> FEATURE:
<221> NAME/KEY: MISC_FEATURE
<222> LOCATION: (9)..(9)
<223> OTHER INFORMATION: Xaa at position 9 = F or Y

<400> SEQUENCE: 17

Gly Gly Ser Ile Ser Xaa Ser Xaa Xaa
1               5

<210> SEQ ID NO 18
<211> LENGTH: 16
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa at position 5 = G or S
<220> FEATURE:
<221> NAME/KEY: MISC_FEATURE
<222> LOCATION: (6)..(6)
<223> OTHER INFORMATION: Xaa at position 6 = E or G
<220> FEATURE:
<221> NAME/KEY: MISC_FEATURE
<222> LOCATION: (7)..(7)
<223> OTHER INFORMATION: Xaa at position 7 = K or I
<220> FEATURE:
<221> NAME/KEY: MISC_FEATURE
<222> LOCATION: (11)..(11)
<223> OTHER INFORMATION: Xaa at position 11 = N or S

<400> SEQUENCE: 18

Ser Phe Tyr Tyr Xaa Xaa Xaa Thr Tyr Xaa Pro Ser Leu Lys Ser
1               5                   10                  15

<210> SEQ ID NO 19
<211> LENGTH: 592
<212> TYPE: PRT
<213> ORGANISM: Mus musculus

<400> SEQUENCE: 19

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Pro Lys Ser Asp
                20                  25                  30

Val Glu Met Glu Ala Gln Lys Asp Ala Ser Ile His Leu Ser Cys Asn
            35                  40                  45

Arg Thr Ile His Pro Leu Lys His Phe Asn Ser Asp Val Met Ala Ser
        50                  55                  60

Asp Asn Gly Gly Ala Val Lys Leu Pro Gln Leu Cys Lys Phe Cys Asp
65                  70                  75                  80

Val Arg Leu Ser Thr Cys Asp Asn Gln Lys Ser Cys Met Ser Asn Cys
                85                  90                  95

Ser Ile Thr Ala Ile Cys Glu Lys Pro His Glu Val Cys Val Ala Val
            100                 105                 110

Trp Arg Lys Asn Asp Lys Asn Ile Thr Leu Glu Thr Val Cys His Asp
        115                 120                 125

Pro Lys Leu Thr Tyr His Gly Phe Thr Leu Glu Asp Ala Ala Ser Pro
    130                 135                 140

Lys Cys Val Met Lys Glu Lys Lys Arg Ala Gly Glu Thr Phe Phe Met
145                 150                 155                 160
```

```
Cys Ala Cys Asn Met Glu Glu Cys Asn Asp Tyr Ile Ile Phe Ser Glu
            165                 170                 175
Glu Tyr Thr Thr Ser Ser Pro Asp Leu Leu Val Ile Ile Gln Val
            180                 185                 190
Thr Gly Val Ser Leu Leu Pro Pro Leu Gly Ile Ala Ile Ala Val Ile
            195                 200                 205
Ile Ile Phe Tyr Cys Tyr Arg Val His Arg Gln Gln Lys Leu Ser Pro
210                 215                 220
Ser Trp Glu Ser Ser Lys Pro Arg Lys Leu Met Asp Phe Ser Asp Asn
225                 230                 235                 240
Cys Ala Ile Ile Leu Glu Asp Asp Arg Ser Asp Ile Ser Ser Thr Cys
            245                 250                 255
Ala Asn Asn Ile Asn His Asn Thr Glu Leu Leu Pro Ile Glu Leu Asp
            260                 265                 270
Thr Leu Val Gly Lys Gly Arg Phe Ala Glu Val Tyr Lys Ala Lys Leu
            275                 280                 285
Lys Gln Asn Thr Ser Glu Gln Phe Glu Thr Val Ala Val Lys Ile Phe
290                 295                 300
Pro Tyr Glu Glu Tyr Ser Ser Trp Lys Thr Glu Lys Asp Ile Phe Ser
305                 310                 315                 320
Asp Ile Asn Leu Lys His Glu Asn Ile Leu Gln Phe Leu Thr Ala Glu
            325                 330                 335
Glu Arg Lys Thr Glu Leu Gly Lys Gln Tyr Trp Leu Ile Thr Ala Phe
            340                 345                 350
His Ala Lys Gly Asn Leu Gln Glu Tyr Leu Thr Arg His Val Ile Ser
            355                 360                 365
Trp Glu Asp Leu Arg Lys Leu Gly Ser Ser Leu Ala Arg Gly Ile Ala
370                 375                 380
His Leu His Ser Asp His Thr Pro Cys Gly Arg Pro Lys Met Pro Ile
385                 390                 395                 400
Val His Arg Asp Leu Lys Ser Ser Asn Ile Leu Val Lys Asn Asp Leu
            405                 410                 415
Thr Cys Cys Leu Cys Asp Phe Gly Leu Ser Leu Arg Leu Asp Pro Thr
            420                 425                 430
Leu Ser Val Asp Asp Leu Ala Asn Ser Gly Gln Val Gly Thr Ala Arg
            435                 440                 445
Tyr Met Ala Pro Glu Val Leu Glu Ser Arg Met Asn Leu Glu Asn Val
450                 455                 460
Glu Ser Phe Lys Gln Thr Asp Val Tyr Ser Met Ala Leu Val Leu Trp
465                 470                 475                 480
Glu Met Thr Ser Arg Cys Asn Ala Val Gly Glu Val Lys Asp Tyr Glu
            485                 490                 495
Pro Pro Phe Gly Ser Lys Val Arg Glu His Pro Cys Val Glu Ser Met
            500                 505                 510
Lys Asp Ser Val Leu Arg Asp Arg Gly Arg Pro Glu Ile Pro Ser Phe
            515                 520                 525
Trp Leu Asn His Gln Gly Ile Gln Ile Val Cys Glu Thr Leu Thr Glu
530                 535                 540
Cys Trp Asp His Asp Pro Glu Ala Arg Leu Thr Ala Gln Cys Val Ala
545                 550                 555                 560
Glu Arg Phe Ser Glu Leu Glu His Pro Glu Arg Leu Ser Gly Arg Ser
            565                 570                 575
Cys Ser Gln Glu Lys Ile Pro Glu Asp Gly Ser Leu Asn Thr Thr Lys
```

<210> SEQ ID NO 20
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Xaa at position 9 = Y or F

<400> SEQUENCE: 20

Arg Ala Ser Gln Ser Val Arg Ser Xaa Leu Ala
1               5                   10

<210> SEQ ID NO 21
<211> LENGTH: 20
<212> TYPE: DNA
<213> ORGANISM: Homo sapiens

<400> SEQUENCE: 21
atggagtttg ggctgagctg                                               20

<210> SEQ ID NO 22
<211> LENGTH: 21
<212> TYPE: DNA
<213> ORGANISM: Homo sapiens

<400> SEQUENCE: 22
tgccaggggg aagaccgatg g                                             21

<210> SEQ ID NO 23
<211> LENGTH: 24
<212> TYPE: DNA
<213> ORGANISM: Homo sapiens

<400> SEQUENCE: 23
atggaaaccc cagcgcagct tctc                                          24

<210> SEQ ID NO 24
<211> LENGTH: 20
<212> TYPE: DNA
<213> ORGANISM: Homo sapiens

<400> SEQUENCE: 24
cgggaagatg aagacagatg                                               20

<210> SEQ ID NO 25
<211> LENGTH: 121
<212> TYPE: PRT
<213> ORGANISM: Homo sapiens

<400> SEQUENCE: 25

Gln Leu Gln Val Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Tyr Phe Ser Trp Gly Trp Ile Arg Gln Pro Pro Gly Lys Gly Leu Glu
        35                  40                  45

Trp Ile Gly Ser Phe Tyr Tyr Gly Glu Lys Thr Tyr Tyr Asn Pro Ser
    50                  55                  60

Leu Lys Ser Arg Ala Thr Ile Ser Ile Asp Thr Ser Lys Ser Gln Phe

```
                 65                  70                  75                  80
Ser Leu Lys Leu Ser Ser Val Thr Ala Ala Asp Thr Ala Val Tyr Tyr
                         85                  90                  95

Cys Pro Arg Gly Pro Thr Met Ile Arg Gly Val Ile Asp Ser Trp Gly
            100                 105                 110

Gln Gly Thr Leu Val Thr Val Ser Ser
            115                 120

<210> SEQ ID NO 26
<211> LENGTH: 363
<212> TYPE: DNA
<213> ORGANISM: Homo sapiens

<400> SEQUENCE: 26
cagctgcagg tgcaggagtc gggcccagga ctggtgaagc cttcggagac cctgtccctc      60
acctgcactg tctctggtgg ctccatcagc aacagttatt ctcctgggg ctggatccgc      120 cagcccccag ggaagggact ggagtggatt gggagtttct attatggtga aaaaacctac     180
tacaacccgt ccctcaagag ccgagccacc atatccattg acacgtccaa gagccagttc     240
tccctgaagc tgagctctgt gaccgccgca gacacggctg tgtattactg ccgagaggg     300 cctactatga ttcggggagt tatagactcc tggggccagg gaaccctggt caccgtctcc    360
tca                                                                    363

<210> SEQ ID NO 27
<211> LENGTH: 107
<212> TYPE: PRT
<213> ORGANISM: Homo sapiens

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 28
<211> LENGTH: 321
<212> TYPE: DNA
<213> ORGANISM: Homo sapiens

<400> SEQUENCE: 28
gaaattgtgt tgacacagtc tccagccacc ctgtctttgt ctccagggga aagagccacc      60
ctctcctgca gggccagtca gagtgttcgc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctccgac gttcggccaa    300
```

```
gggaccaagg tggaaatcaa a                                          321
```

\<210\> SEQ ID NO 29
\<211\> LENGTH: 236
\<212\> TYPE: PRT
\<213\> ORGANISM: Artificial
\<220\> FEATURE:
\<223\> OTHER INFORMATION: Synthetic

\<400\> SEQUENCE: 29

```
Ala Ala Thr Met Gly Trp Ser Cys Ile Ile Leu Phe Leu Val Ala Thr
1               5                   10                  15

Ala Thr Gly Val His Ser Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Arg Ser Phe Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Pro Thr Phe Gly Gln Gly Thr Lys Val Glu Ile
        115                 120                 125

Lys Gly Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

\<210\> SEQ ID NO 30
\<211\> LENGTH: 470
\<212\> TYPE: PRT
\<213\> ORGANISM: Artificial
\<220\> FEATURE:
\<223\> OTHER INFORMATION: Synthetic

\<400\> SEQUENCE: 30

```
Met Gly Trp Ser Cys Ile Ile Leu Phe Leu Val Ala Thr Ala Thr Gly
1               5                   10                  15

Val His Ser Gln Leu Gln Val Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Asn Ser Tyr Phe Ser Trp Gly Trp Ile Arg Gln Pro Pro Gly Lys
    50                  55                  60

Gly Leu Glu Trp Ile Gly Ser Phe Tyr Tyr Gly Glu Lys Thr Tyr Tyr
```

```
                65                  70                  75                  80
Asn Pro Ser Leu Lys Ser Arg Ala Thr Ile Ser Ile Asp Thr Ser Lys
                    85                  90                  95
Ser Gln Phe Ser Leu Lys Leu Ser Ser Val Thr Ala Ala Asp Thr Ala
                100                 105                 110
Val Tyr Tyr Cys Pro Arg Gly Pro Thr Met Ile Arg Gly Val Ile Asp
                115                 120                 125
Ser Trp Gly Gln Gly Thr Leu Val Thr Val Ser Ala Ser Thr Lys
        130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                    165                 170                 175
Val Thr Val Ser Trp Asn Ser Gly Ala Leu Thr Ser Gly Val His Thr
                    180                 185                 190
Phe Pro Ala Val Leu Gln Ser Ser Gly Leu Tyr Ser Leu Ser Ser Val
                195                 200                 205
Val Thr Val Pro Ser Ser Ser Leu Gly Thr Gln Thr Tyr Ile Cys Asn
        210                 215                 220
Val Asn His Lys Pro Ser Asn Thr Lys Val Asp Lys Arg Val Glu Pro
225                 230                 235                 240
Lys Ser Cys Asp Lys Thr His Thr Cys Pro Pro Cys Pro Ala Pro Glu
                    245                 250                 255
Leu Leu Gly Gly Pro Ser Val Phe Leu Phe Pro Pro Lys Pro Lys Asp
                    260                 265                 270
Thr Leu Met Ile Ser Arg Thr Pro Glu Val Thr Cys Val Val Val Asp
                275                 280                 285
Val Ser His Glu Asp Pro Glu Val Lys Phe Asn Trp Tyr Val Asp Gly
        290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                    325                 330                 335
Leu Asn Gly Lys Glu Tyr Lys Cys Lys Val Ser Asn Lys Ala Leu Pro
                    340                 345                 350
Ala Pro Ile Glu Lys Thr Ile Ser Lys Ala Lys Gly Gln Pro Arg Glu
                355                 360                 365
Pro Gln Val Tyr Thr Leu Pro Pro Ser Arg Glu Glu Met Thr Lys Asn
        370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                    405                 410                 415
Thr Pro Pro Val Leu Asp Ser Asp Gly Ser Phe Phe Leu Tyr Ser Lys
                    420                 425                 430
Leu Thr Val Asp Lys Ser Arg Trp Gln Gln Gly Asn Val Phe Ser Cys
                435                 440                 445
Ser Val Met His Glu Ala Leu His Asn His Tyr Thr Gln Lys Ser Leu
        450                 455                 460
Ser Leu Ser Pro Gly Lys
465                 470

<210> SEQ ID NO 31
<211> LENGTH: 470
```

<212> TYPE: PRT
<213> ORGANISM: Artificial
<220> FEATURE:
<223> OTHER INFORMATION: Synthetic

<400> SEQUENCE: 31

Met Gly Trp Ser Cys Ile Ile Leu Phe Leu Val Ala Thr Ala Thr Gly
1               5                   10                  15

Val His Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Ser Tyr Ser Trp Gly Trp Ile Arg Gln Pro Pro Gly Lys
    50                  55                  60

Gly Leu Glu Trp Ile Gly Ser Phe Tyr Tyr Ser Gly Ile Thr Tyr Tyr
65                  70                  75                  80

Ser Pro Ser Leu Lys Ser Arg Ile Ile Ile Ser Glu Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Ser Gly Phe Thr Met Ile Arg Gly Ala Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile

```
                    385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 32
<211> LENGTH: 236
<212> TYPE: PRT
<213> ORGANISM: Artificial
<220> FEATURE:
<223> OTHER INFORMATION: Synthetic

<400> SEQUENCE: 32

Ala Ala Thr Met Gly Trp Ser Cys Ile Ile Leu Phe Leu Val Ala Thr
1               5                   10                  15

Ala Thr Gly Val His Ser Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Arg Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Pro Thr Phe Gly Gln Gly Thr Lys Val Glu Ile
        115                 120                 125

Lys Gly Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 33
<211> LENGTH: 121
<212> TYPE: PRT
<213> ORGANISM: Homo sapiens

<400> SEQUENCE: 33
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Ser Trp Gly Trp Ile Arg Gln Pro Pro Gly Lys Gly Leu Glu
        35                  40                  45

Trp Ile Gly Ser Phe Tyr Tyr Ser Gly Ile Thr Tyr Tyr Ser Pro Ser
    50                  55                  60

Leu Lys Ser Arg Ile Ile Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Gly Phe Thr Met Ile Arg Gly Ala Leu Asp Tyr Trp Gly
            100                 105                 110

Gln Gly Thr Leu Val Thr Val Ser Ser
            115                 120
```

<210> SEQ ID NO 34
<211> LENGTH: 363
<212> TYPE: DNA
<213> ORGANISM: Homo sapiens

<400> SEQUENCE: 34

```
cagctacagc tgcaggagtc gggcccagga ctggtgaagc cttcggagac cctatccctc    60
acctgcactg tctctggtgg ctccatcagc agtagtagtt actcctgggg ctggatccgc   120
cagcccccag ggaagggcct ggagtggatt gggagtttct attacagtgg gatcacctac   180
tacagcccgt ccctcaagag tcgaattatc atatccgaag acacgtccaa gaaccagttc   240
tccctgaagc tgagttctgt gaccgccgca gacacggctg tgtattactg tgcgagcggg   300
tttactatga ttcggggagc ccttgactac tggggccagg gaaccctggt caccgtctcc   360
tca                                                                 363
```

<210> SEQ ID NO 35
<211> LENGTH: 107
<212> TYPE: PRT
<213> ORGANISM: Homo sapiens

<400> SEQUENCE: 35

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 36
<211> LENGTH: 321
<212> TYPE: DNA
<213> ORGANISM: Homo sapiens

<400> SEQUENCE: 36

```
gaaattgtgt tgacacagtc tccagccacc ctgtctttgt ctccagggga aagagccacc    60
ctctcctgca gggccagtca gagtgttaga agtttcttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgac gttcggccaa   300
gggaccaagg tggaaatcaa a                                             321
```

<210> SEQ ID NO 37
<211> LENGTH: 451
<212> TYPE: PRT
<213> ORGANISM: Artificial
<220> FEATURE:
<223> OTHER INFORMATION: Synthetic

<400> SEQUENCE: 37

```
Gln Leu Gln Val Gln Glu Ser Gly Pro Gly Leu Val Lys Pro Ser Glu
 1               5                  10                  15

Thr Leu Ser Leu Thr Cys Thr Val Ser Gly Gly Ser Ile Ser Asn Ser
            20                  25                  30

Tyr Phe Ser Trp Gly Trp Ile Arg Gln Pro Pro Gly Lys Gly Leu Glu
        35                  40                  45

Trp Ile Gly Ser Phe Tyr Tyr Gly Glu Lys Thr Tyr Tyr Asn Pro Ser
    50                  55                  60

Leu Lys Ser Arg Ala Thr Ile Ser Ile Asp Thr Ser Lys Ser Gln Phe
65                  70                  75                  80

Ser Leu Lys Leu Ser Ser Val Thr Ala Ala Asp Thr Ala Val Tyr Tyr
                85                  90                  95

Cys Pro Arg Gly Pro Thr Met Ile Arg Gly Val Ile Asp Ser Trp Gly
           100                 105                 110

Gln Gly Thr Leu Val Thr Val Ser Ser Ala Ser Thr Lys Gly Pro Ser
       115                 120                 125

Val Phe Pro Leu Ala Pro Ser Ser Lys Ser Thr Ser Gly Gly Thr Ala
   130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
```

```
                290                295                300
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 38
<211> LENGTH: 1413
<212> TYPE: DNA
<213> ORGANISM: Artificial
<220> FEATURE:
<223> OTHER INFORMATION: Synthetic

<400> SEQUENCE: 38
atgggatggt catgtatcat ccttttttcta gtagcaactg caactggagt acattcacag     60
ctgcaggtgc aggagtcggg cccaggactg gtgaagcctt cggagaccct gtccctcacc    120
tgcactgtct ctggtggctc catcagcaac agttatttct cctggggctg atccgccag    180 cccccaggga agggactgga gtggattggg agtttctatt atggtgaaaa aacctactac    240
aacccgtccc tcaagagccg agccaccata tccattgaca cgtccaagag ccagttctcc    300
ctgaagctga gctctgtgac cgccgcagac acggctgtgt attactgtcc gagagggcct    360
actatgattc ggggagttat agactcctgg ggccagggaa ccctggtcac cgtctcctca    420
gctagcacca agggcccatc ggtcttcccc ctggcaccct cctccaagag cacctctggg    480
ggcacagcgg ccctgggctg cctggtcaag gactacttcc ccgaaccggt gacggtgtcg    540
tggaactcag gcgccctgac cagcggcgtg cacaccttcc cggctgtcct acagtcctca    600
ggactctact ccctcagcag cgtggtgacc gtgccctcca gcagcttggg cacccagacc    660
tacatctgca acgtgaatca caagcccagc aacaccaagg tggacaagag agttgagccc    720
aaatcttgtg acaaaactca cacatgccca ccgtgcccag cacctgaact cctggggga    780 ccgtcagtct tcctcttccc cccaaaaccc aaggacaccc tcatgatctc ccggaccct    840 gaggtcacat gcgtggtggt ggacgtgagc cacgaagacc ctgaggtcaa gttcaactgg    900
tatgtggacg gcgtggaggt gcataatgcc aagacaaagc cgcgggagga gcagtacaac    960
agcacgtacc gtgtggtcag cgtcctcacc gtcctgcacc aagactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggaggag   1140
```

| | |
|---|---|
| atgaccaaga accaagtcag cctgacctgc ctggtcaaag gcttctatcc cagcgacatc | 1200 |
| gccgtggagt gggagagcaa tgggcagccg agaacaact acaagaccac gcctcccgtg | 1260 |
| ctggactccg acggctcctt cttcctctat tccaagctca ccgtggacaa gagcaggtgg | 1320 |
| cagcagggga acgtcttctc atgctccgtg atgcatgagg ctctgcacaa ccactacacg | 1380 |
| cagaagagcc tctccctgtc tccgggcaaa tga | 1413 |

<210> SEQ ID NO 39
<211> LENGTH: 4702
<212> TYPE: DNA
<213> ORGANISM: Mus musculus

<400> SEQUENCE: 39

| | |
|---|---|
| gagtcactcg cgcgcaccga ccgacgacac ccctcgcgcg cgcacacgct cgcctggggg | 60 |
| acggagcccc agcctcctgc tcagctctcc tcggccgccg ggggcctcct ccgggcctcc | 120 |
| gagctccggg gatcgccggc cacatctggc ccgcatcctg agaggcgag gagtaaaggc | 180 |
| gcagcccggg gtccccgagg ctcggttcgt ggcgcaccag gggccggtct atgacgagcg | 240 |
| acggggctg ccatgggtcg ggggctgctc cggggcctgt ggccgctgca tatcgtcctg | 300 |
| tggacgcgca tcgccagcac gatcccgccg cacgttccca agtcggatgt ggaaatggaa | 360 |
| gcccagaaag atgcatccat ccacgtaagc tgtaatagga ccatccatcc actgaaacat | 420 |
| tttaacagtg atgtcatggc cagcgacaat ggcggtgcgg tcaagcttcc acagctgtgc | 480 |
| aagttttgcg atgtgagact gtccactttgc gacaaccaga agtcctgcat gagcaactgc | 540 |
| agcatcacgg ccatctgtga aagccgcat gaagtctgcg tggccgtgtg gaggaagaac | 600 |
| gacaagaaca ttactctgga gacggtttgc cacgaccca agctcaccta ccacggcttc | 660 |
| actctggaag atgccgcttc tcccaagtgt gtcatgaagg aaaagaaaag ggcgggcgag | 720 |
| actttcttca tgtgtgcctg taacatgaa gagtgcaacg attacatcat cttttcggaa | 780 |
| gaatacacca ccagcagtcc cgacctgttg ttggtcatta tccaagtgac gggtgtcagc | 840 |
| ctcctgcctc cgctggggat tgccatagct gtcatcatca tcttctactg ctaccgtgtc | 900 |
| caccggcagc agaagctgag cccgtcctgg gagagcagca agcccggaa actgatggat | 960 |
| ttcagtgaca attgtgccat catcctggag gacgaccgct ccgacatcag ctccacgtgc | 1020 |
| gccaacaaca tcaaccacaa cacggagctg ctgcccatcg agctggacac gctggtgggg | 1080 |
| aagggccgct tcgccgaggt ctacaaggcc aagctgaagc agaacacctc agagcagttt | 1140 |
| gagaccgtgg ctgtcaagat cttccccttac gaggagtact cctcgtggaa acagagaag | 1200 |
| gacatcttct ccgatatcaa cctgaagcat gagaacatcc tgcagttcct gacggccgag | 1260 |
| gagcggaaga cagagctggg caagcagtac tggctgatca cggcgttcca cgcgaagggc | 1320 |
| aacctgcagg agtacctcac gaggcatgtc atcagctggg aggacctgag gaagctgggc | 1380 |
| agctccctgg cccggggcat cgctcatctc cacagtgacc acactccttg tgggaggccc | 1440 |
| aagatgccca ttgttcacag ggacctcaag agctctaaca tcctagtgaa gaacgacttg | 1500 |
| acctgttgcc tgtgtgactt cgggctgtcc ttgcgcctgg accctactct gtctgtggat | 1560 |
| gacctggcca acagcgggca ggtgggaacg gcaagataca tggccccgga agttctagaa | 1620 |
| tccaggatga atctggaaaa cgtggagtcg ttcaagcaga cggatgtcta ctccatggct | 1680 |
| ctggtactct gggaaatgac gtcccgctgc aatgctgtgg agaagtgaa ggattacgag | 1740 |
| cccccatttg gttccaaggt gcgggagcac ccctgtgtgg agagcatgaa agacagtgtg | 1800 |
| ctgagagacc gagggcggcc ggaaattccc agcttctggc tcaaccacca gggcatccag | 1860 |

```
atcgtgtgtg agactttgac cgagtgctgg gaccatgacc ccgaagcccg tctcacagca  1920
cagtgtgtgg cagagcgctt cagtgagctg gagcatccgg agagactctc tgggaggagc  1980
tgctcccagg agaagattcc agaagatggc tcgctgaaca ctaccaaata gctttttctg  2040
ggcaggctgg gccaagcctc cagaagccgt cctctagcca agaccagag gcagcaggat  2100
tctctcctga ctgatgcttc tggaaaacca aggacttgct cccttcttcc ccaggagctg  2160
ccccgtgttt agaagcggca gcagcagcag caacaaccat agcggcggtg gcagcggcgg  2220
gggatgagtg acagagagcg tcctatgcct tggagactgt catggcataa gctgtgctag  2280
cacctcctca ggaaatgaga ttgattttta caacagccaa taacgtttgc actttattaa  2340
tgcctgtgtg taaatacgaa tagctatgtt ttatatatat ctatatatct atatgtctat  2400
atctctctat atatagccat actctgcaag gagacaaaga aaatgatcaa atgtgttccc  2460
cggggaatta gttttttattg gagagctcta gaatggagca aagggactc gggatagcgt  2520
tagcacttga caatcagtca cacaagcaac gatcccctga cagcagggtt gggggcacaa  2580
ttgtatgaga aggatccatg ccttgcagcc tgctttggcc acaaaacact ttgttttgca  2640
ataatgaccc tctacagtag ggtgctttat ggaccaggga gctgagctcc agtccagcac  2700
tgagtcccag gatctcccat gtgtctttgc ttctcttggt tgttatcttt gacattcaag  2760
ccccactctg acttgtgaac cttctgactt agccttgaaa cttggcccca ttttctgct  2820
tttacgggct accaaaaatc aaagaagacc gttccccacc catgaaattg gcctaccatc  2880
tactaataag attgagttct tgatcctttt cctgtgcata agtaactgtt atttgttccc  2940
tgccattatc ctttgttgat ttttttaaaa caaggcacac cctacactca gcccctcagc  3000
ctcactgtgt ttaattttttg tcgctctgct gctgggtctt ccagcttgcc atggcaacac  3060
cagtgggttc cattatccca gcctcccaaa tagcggacag gatttgaatg cgcacgctg  3120
cccatactgt acagctgtgt ccggggactc tttgaaccct ccttttcctc gatcaacaca  3180
ctgtcgaaaa agttagttga gcttctttag aactatttgg gaggttgcag agaagcttag  3240
attccccaat aagcagagga ggtggttcct agctccgccc ccaggggca tcatttccag  3300
caagaagggc atggctgcag ctgcctcact gctcactcct aagcctccag acttcccatt  3360
actcacaccc accccagtct ggaaatgaaa gctgcttcca gtcaggatcc attgtaagaa  3420
aagtgcgttc gtgagcatgg agagatagca agtaaaaatg gttgcaccac aagcaagacg  3480
acctgagttc aaccccctcca gaacccacga caaaagtcat gttcagtggg gcactcttat  3540
catctcagcc ctgggaagac gaacacccct ggaagcccag ggctaggaag attgtctcca  3600
aagcagggtg agcagcaccc tgaggaacat ctgacattga ctgacttctg gtctccatca  3660
caggtgcacc cacgaacacc cacacacacg tgcacacact agaaatgtgc attcatttca  3720
ccctgttctg ggaacagatt ggattgcaca aaacttatct gatgttatga tttgaaattg  3780
acataaattg gacatcagga gaccacctgt gtgtgacctc attaggtcag ggctcttgt  3840
atgcataata agtttcatct gcctctgcaa gggaacctct ctgctctaag aatctttctt  3900
tatggctact ggtctctgca tggtcctaac cttggcagaa attacaagtg catatttgaa  3960
caggggtcac acaggactcc tgtgtagaga cagggactct gtgtccactt ggatgagagc  4020
agggaatgag ctttaaaagg aaacttgtta atccccccaac aaatgtggat gttgcaaacc  4080
aaagtctgtc ttgttaagaa attgtgtttt tgaagcgact tattttcaac caaataggag  4140
catgattgga gaaccaccaa gggggccttt tgttctgttt ggtcaacatg gtcaaattgg  4200
gggtaggaca aaaatctatg tgttctgtgg cttcgaacac catggaaacc cccaagccca  4260
```

| | |
|---|---|
| cttgcttctt ttggattgcc agtgctaacc cagtagctgt tgttcaccgc cctctagcgg | 4320 |
| ggaatttaca gaatgctggt ccactagtgg gatttctagg gttcaaaagt gacttcactt | 4380 |
| ccgggtcatc atcagaaact ggaatatggt gtcatgttac tgtggcttgt tttgtttatg | 4440 |
| tcatttcttt tctttattca agaaaaagac caaggaatag catcgctgtc attcctcaaa | 4500 |
| gtgttgactc ttgttcacta ctctacataa agggaaagtt ttattctttt attgaacact | 4560 |
| tcggccatat tcatgtattc aaataggaat gtgaatgaat gcacaatatt cttttttatat | 4620 |
| caaaacctaa agcacttatt ttcaatctat gcagtgtttg tcttttatat aaataaaaat | 4680 |
| gtctagtaga tcaaataaat cc | 4702 |

<210> SEQ ID NO 40
<211> LENGTH: 4704
<212> TYPE: DNA
<213> ORGANISM: Homo sapiens

<400> SEQUENCE: 40

| | |
|---|---|
| ggagagggag aaggctctcg ggcggagaga ggtcctgccc agctgttggc gaggagtttc | 60 |
| ctgtttcccc cgcagcgctg agttgaagtt gagtgagtca ctcgcgcgca cggagcgacg | 120 |
| acacccccgc gcgtgcaccc gctcgggaca ggagccggac tcctgtgcag cttccctcgg | 180 |
| ccgccggggg cctccccgcg cctcgccggc ctccaggccc cctcctggct ggcgagcggg | 240 |
| cgccacatct ggcccgcaca tctgcgctgc cggcccggcg cggggtccgg agagggcgcg | 300 |
| gcgcggaggc gcagccaggg gtccgggaag gcgccgtccg ctgcgctggg ggctcggtct | 360 |
| atgacgagca gcggggtctg ccatgggtcg ggggctgctc aggggcctgt ggccgctgca | 420 |
| catcgtcctg tggacgcgta tcgccagcac gatcccaccg cacgttcaga agtcggatgt | 480 |
| ggaaatggag gcccagaaag atgaaatcat ctgccccagc tgtaatagga ctgcccatcc | 540 |
| actgagacat attaataacg acatgatagt cactgacaac aacggtgcag tcaagttttcc | 600 |
| acaactgtgt aaattttgtg atgtgagatt ttccacctgt gacaaccaga aatcctgcat | 660 |
| gagcaactgc agcatcacct ccatctgtga aagccacag gaagtctgtg tggctgtatg | 720 |
| gagaaagaat gacgagaaca taacactaga gacagtttgc catgaccccca agctcccccta | 780 |
| ccatgacttt attctggaag atgctgcttc tccaaagtgc attatgaagg aaaaaaaaaa | 840 |
| gcctggtgag actttcttca tgtgttcctg tagctctgat gagtgcaatg acaacatcat | 900 |
| cttctcagaa gaatataaca ccagcaatcc tgacttgttg ctagtcatat ttcaagtgac | 960 |
| aggcatcagc ctcctgccac cactgggagt tgccatatct gtcatcatca tcttctactg | 1020 |
| ctaccgcgtt aaccggcagc agaagctgag ttcaacctgg gaaaccggca agacgcggaa | 1080 |
| gctcatggag ttcagcgagc actgtgccat catcctggaa gatgaccgct ctgacatcag | 1140 |
| ctccacgtgt gccaacaaca tcaaccacaa cacagagctg ctgcccattg agctggacac | 1200 |
| cctggtgggg aaaggtcgct ttgctgaggt ctataaggcc aagctgaagc agaacacttc | 1260 |
| agagcagttt gagacagtgg cagtcaagat cttttcccctat gaggagtatg cctcttggaa | 1320 |
| gacagagaag gacatcttct cagacatcaa tctgaagcat gagaacatac tccagttcct | 1380 |
| gacggctgag gagcggaaga cggagttggg gaaacaatac tggctgatca ccgccttcca | 1440 |
| cgccaagggc aacctacagg agtacctgac gcggcatgtc atcagctggg aggacctgcg | 1500 |
| caagctgggc agctccctcg cccgggggat tgctcacctc cacagtgatc acactccatg | 1560 |
| tgggaggccc aagatgccca tcgtgcacag ggacctcaag agctccaata tcctcgtgaa | 1620 |
| gaacgaccta acctgctgcc tgtgtgactt tgggctttcc ctgcgtctgg accctactct | 1680 |

```
gtctgtggat gacctggcta acagtgggca ggtgggaact gcaagataca tggctccaga   1740
agtcctagaa tccaggatga atttggagaa tgttgagtcc ttcaagcaga ccgatgtcta   1800
ctccatggct ctggtgctct gggaaatgac atctcgctgt aatgcagtgg gagaagtaaa   1860
agattatgag cctccatttg gttccaaggt gcgggagcac ccctgtgtcg aaagcatgaa   1920
ggacaacgtg ttgagagatc gagggcgacc agaaattccc agcttctggc tcaaccacca   1980
gggcatccag atggtgtgtg agacgttgac tgagtgctgg gaccacgacc cagaggcccg   2040
tctcacagcc cagtgtgtgg cagaacgctt cagtgagctg gagcatctgg acaggctctc   2100
ggggaggagc tgctcggagg agaagattcc tgaagacggc tccctaaaca ctaccaaata   2160
gctcttctgg ggcaggctgg gccatgtcca agaggctgc ccctctcacc aaagaacaga   2220
ggcagcagga agctgcccct gaactgatgc ttcctggaaa accaagggg tcactcccct   2280 ccctgtaagc tgtggggata agcagaaaca acagcagcag ggagtgggtg acatagagca   2340
ttctatgcct ttgacattgt cataggataa gctgtgttag cacttcctca ggaaatgaga   2400 ttgatttta caatagccaa taacatttgc actttattaa tgcctgtata taaatatgaa   2460
tagctatgtt ttatatatat atatatat ctatatatgt ctatagctct atatatatag   2520
ccataccttg aaaagagaca aggaaaaaca tcaaatattc ccaggaaatt ggttttattg   2580
gagaactcca gaaccaagca gagaaggaag ggacccatga cagcattagc atttgacaat   2640
cacacatgca gtggttctct gactgtaaaa cagtgaactt tgcatgagga aagaggctcc   2700
atgtctcaca gccagctatg accacattgc acttgctttt gcaaataat cattccctgc   2760 ctagcacttc tcttctggcc atggaactaa gtacagtggc actgtttgag gaccagtgtt   2820 cccgggttc ctgtgtgccc ttatttctcc tggacttttc atttaagctc caagccccaa   2880
atctgggggg ctagtttaga aactctccct caacctagtt tagaaactct accccatctt   2940
taataccttg aatgttttga accccacttt ttaccttcat gggttgcaga aaatcagaa   3000 cagatgtccc catccatgcg attgcccac catctactaa tgaaaaattg ttcttttttt   3060
catctttccc ctgcacttat gttactattc tctgctccca gccttcatcc tttttctaaaa   3120 aggagcaaat tctcactcta ggctttatcg tgtttacttt ttcattacac ttgacttgat   3180
tttctagttt tctatacaaa caccaatggg ttccatcttt ctgggctcct gattgctcaa   3240
gcacagtttg gcctgatgaa gaggatttca actacacaat actatcattg tcaggactat   3300
gacctcaggc actctaaaca tatgttttgt ttggtcagca cagcgtttca aaaagtgaag   3360
ccactttata aatatttgga gattttgcag gaaaatctgg atccccaggt aaggatagca   3420
gatggttttc agttatctcc agtccacgtt cacaaaatgt gaaggtgtgg agacacttac   3480
aaagctgcct cacttctcac tgtaaacatt agctctttcc actgcctacc tggaccccag   3540
tctaggaatt aaatctgcac ctaaccaagg tcccttgtaa gaaatgtcca ttcaagcagt   3600
cattctctgg gtatataata tgattttgac taccttatct ggtgttaaga tttgaagttg   3660
gccttttatt ggactaaagg ggaactcctt taagggtctc agttagccca gtttctttt   3720 gcttatatgt taatagtttt accctctgca ttggagagag gagtgcttta ctccaagaag   3780 cttt cctcat ggttaccgtt ctctccatca tgccagcctt ctcaaccttt gcagaaatta   3840
ctagagagga tttgaatgtg ggacacaaag gtcccatttg cagttagaaa atttgtgtcc   3900
acaaggacaa gaacaaagta tgagctttaa aactccatag gaaacttgtt aatcaacaaa   3960
gaagtgttaa tgctgcaagt aatctctttt ttaaaacttt ttgaagctac ttattttcag   4020
ccaaatagga atattagaga gggactggta gtgagaatat cagctctgtt tggatggtgg   4080
```

```
aaggtctcat ttattgaga ttttaagat acatgcaaag gtttggaaat agaacctcta    4140
ggcaccctcc tcagtgtggg tgggctgaga gttaaagaca gtgtggctgc agtagcatag    4200
aggcgcctag aaattccact tgcaccgtag ggcatgctga taccatccca atagctgttg    4260
cccattgacc tctagtggtg agtttctaga atactggtcc attcatgaga tattcaagat    4320
tcaagagtat tctcacttct gggttatcag cataaactgg aatgtagtgt cagaggatac    4380
tgtggcttgt tttgtttatg ttttttttc ttattcaaga aaaagacca aggaataaca    4440 ttctgtagtt cctaaaaata ctgactttt tcactactat acataaaggg aaagttttat    4500
tcttttatgg aacacttcag ctgtactcat gtattaaaat aggaatgtga atgctatata    4560 ctcttttat atcaaaagtc tcaagcactt atttttattc tatgcattgt ttgtctttta    4620
cataaataaa atgtttatta gattgaataa agcaaaatac tcaggtgagc atcctgcctc    4680
ctgttcccat tcctagtagc taaa                                          4704
```

<210> SEQ ID NO 41
<211> LENGTH: 161
<212> TYPE: PRT
<213> ORGANISM: Mus musculus

<400> SEQUENCE: 41

```
Ile Pro Pro His Val Pro Lys Ser Asp Val Glu Met Glu Ala Gln Lys
1               5                   10                  15

Asp Ala Ser Ile His Leu Ser Cys Asn Arg Thr Ile His Pro Leu Lys
            20                  25                  30

His Phe Asn Ser Asp Val Met Ala Ser Asp Asn Gly Gly Ala Val Lys
        35                  40                  45

Leu Pro Gln Leu Cys Lys Phe Cys Asp Val Arg Leu Ser Thr Cys Asp
    50                  55                  60

Asn Gln Lys Ser Cys Met Ser Asn Cys Ser Ile Thr Ala Ile Cys Glu
65                  70                  75                  80

Lys Pro His Glu Val Cys Val Ala Val Trp Arg Lys Asn Asp Lys Asn
                85                  90                  95

Ile Thr Leu Glu Thr Val Cys His Asp Pro Lys Leu Thr Tyr His Gly
            100                 105                 110

Phe Thr Leu Glu Asp Ala Ala Ser Pro Lys Cys Val Met Lys Glu Lys
        115                 120                 125

Lys Arg Ala Gly Glu Thr Phe Phe Met Cys Ala Cys Asn Met Glu Glu
    130                 135                 140

Cys Asn Asp Tyr Ile Ile Phe Ser Glu Glu Tyr Thr Thr Ser Ser Pro
145                 150                 155                 160

Asp
```

<210> SEQ ID NO 42
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa at position 2 = P or F
<220> FEATURE:
<221> NAME/KEY: MISC_FEATURE
<222> LOCATION: (8)..(8)
<223> OTHER INFORMATION: Xaa at position 8 = V or A
<220> FEATURE:
<221> NAME/KEY: MISC_FEATURE
<222> LOCATION: (9)..(9)

```
<223> OTHER INFORMATION: Xaa at position 9 = I or L
<220> FEATURE:
<221> NAME/KEY: MISC_FEATURE
<222> LOCATION: (11)..(11)
<223> OTHER INFORMATION: Xaa at position 11 = S or Y

<400> SEQUENCE: 42

Gly Xaa Thr Met Ile Arg Gly Xaa Xaa Asp Xaa
1               5                   10
```

ANTI-TGF-BETA RECEPTOR II ANTIBODIES

This application claims priority to U.S. provisional application No. 61/198,697 filed Nov. 7, 2008 and U.S. provisional application No. 61/170,369 filed Apr. 17, 2009.

The present invention is in the field of medicine, particularly in the field of antibodies that bind human transforming growth factor beta receptor II (TGFβRII), pharmaceutical compositions comprising antibodies and methods of using the antibodies, for example, for treating cancer, fibrosis, and fibrotic diseases.

TGFβs are pleiotropic cytokines that regulate cell growth and differentiation, motility, extracellular matrix production, and immune functions. TGFβs have three mammalian isoforms, TGFβ-1, TGFβ-2 and TGFβ-3, each with distinct functions in vivo. All three TGFβs use the same receptor signaling system. The binding of TGFβs to TGFβRII is a crucial step in initiating activation of the TGFβ signaling pathway, leading to phosphorylation of Smad2, and translocation of the activated Smad2/Smad4 complex to the nucleus to modulate gene expression.

Human monoclonal antibodies (mAbs) that bind human TGFβRII with high affinity ($K_D$ of $8.06\times10^{-10}$ and $1.91\times10^{-9}$ M) to treat kidney disease and tissue fibrosis are disclosed in JP 2004/121001A. The application also discloses that the mAbs suppress the TGFβ-induced growth of keratinocytes (average value of $IC_{50}$ of 2.17-3.89, 3.17-4.95, and 3.21-5.07 µg/ml). Use of a fully human monoclonal antibody to TGFβRII was reported to be effective to reduce the deposit of extracellular matrix in rat anti-Thy-1 nephritis. (Kasuga, H., et al., Kidney Int'l, Vol. 60 (2001) 1745-1755.)

To date, there has been no disclosure of highly specific, high affinity anti-TGFβRII antibodies that specifically bind the extracellular domain of human TGFβRII with very high affinity, block the binding of human TGFβ1, TGFβ2, and TGFβ3 to human TGFβRII, inhibit angiogenesis, suppress tumor cell growth, inhibit migration and invasion of cancer cells, reduce collagen deposition and liver function, inhibit ligand induced regulation of T cells, or inhibit tumor growth in combination with cytotoxic agents, and are therefore needed.

The present invention seeks to provide novel isolated anti-TGFβRII mAbs that address these needs. The TGF beta RII is mammalian, and is preferably human. The antibodies of the present invention are capable of one or more of the following activities: 1) displaying high affinity binding toward the extracellular domain of human TGFβRII; 2) blocking the binding of TGFβRII ligands (TGFβ1, TGFβ2, and TGFβ3) to TGFβRII, thereby inhibiting TGFβ-induced Smad2 phosphorylation; 3) internalizing TGFβRII, which can act as a signaling down-regulation mechanism independent of ligand-receptor interaction; 4) inhibiting ligand-induced TGFβRII signaling pathways; 5) inhibiting TGFβRII-mediated cellular activities; 6) inhibiting tumor growth in vitro and in vivo; and also more preferably are additionally capable of one or more of the following: 7) inhibiting angiogenesis by reducing TGFβ-induced vascular endothelial growth factor A (VEGF-A) secretion; 8) inhibiting migration and invasion of cancer cells, 9) reducing collagen deposition and liver function; 10) inhibiting ligand induced regulation of T cells to form Treg cells that have immunosuppressive effects; or 11) inhibiting tumor growth in combination with cytotoxic agents.

A high affinity monoclonal antibody that specifically binds to TGFβRII and neutralizes TGFβRII-mediated activity would be particularly useful as a therapeutic bioagent for the treatment of TGFβ signaling mediated diseases.

According to a first aspect of the present invention, there is provided isolated antibodies that specifically bind the extracellular domain of human TGFβRII with a $K_D$ of less than 100 pM at room temperature (20-25° C.).

In one aspect, the antibodies of the present invention block binding of human TGFβ1, TGFβ2, or TGFβ3 to human TGFβRII with an $IC_{50}$ of less than 1.0 nM as determined by ELISA.

In another aspect, the antibodies of the present invention inhibit TGFβ-induced Smad2 phosphorylation with an $IC_{50}$ of less than 30 nM.

In yet another aspect, the antibodies of the present invention comprise an antibody that specifically binds to TGFβRII comprising:
i) a CDRH1 having the sequence GGSISNSYF (SEQ ID NO: 1), a CDRH2 having the sequence SFYYGEKTYYNPSLKS (SEQ ID NO: 2), a CDRH3 having the sequence GPTMIRGVIDS (SEQ ID NO: 3), a CDRL1 having the sequence RASQSVRSYLA (SEQ ID NO: 10), a CDRL2 having the sequence DASNRAT (SEQ ID NO: 11), and a CDRL3 having the sequence QQRSNWPPT (SEQ ID NO: 12); or
ii) a CDRH1 having the sequence GGSISSSSY (SEQ ID NO: 7), a CDRH2 having the sequence SFYYSGITYYSPSLKS (SEQ ID NO: 8), a CDRH3 having the sequence GFTMIRGALDY (SEQ ID NO: 9), a CDRL1 having the sequence RASQSVRSFLA (SEQ ID NO: 16), a CDRL2 having the sequence DASNRAT (SEQ ID NO: 11), and a CDRL3 having the sequence QQRSNWPPT (SEQ ID NO: 12).

In another aspect, the antibodies of the present invention comprise:
i) a HCVR amino acid sequence:

(SEQ ID NO: 25)
QLQVQESGPGLVKPSETLSLTCTVSGGSISNSYFSWGWIRQPPGKG

LEWIGSFYYGEKTYYNPSLKSRATISIDTSKSQFSLKLSSVTAADTA

VYYCPRGPTMIRGVIDSWGQGTLVTVSS and a LCVR amino acid sequence:

(SEQ ID NO: 27)
EIVLTQSPATLSLSPGERATLSCRASQSVRSYLAWYQQKPGQAPRLLIYD

ASNRATGIPARFSGSGSGTDFTLTISSLEPEDFAVYYCQQRSNWPPTFGQ

GTKVEIK;

or ii) a HCVR amino acid sequence:

(SEQ ID NO: 33)
QLQLQESGPGLVKPSETLSLTCTVSGGSISSSSYSWGWIRQPPGKGL

EWIGSFYYSGITYYSPSLKSRIIISEDTSKNQFSLKLSSVTAADTAVY

YCASGFTMIRGALDYWGQGTLVTVSS, and a LCVR amino acid sequence:

(SEQ ID NO: 35)
EIVLTQSPATLSLSPGERATLSCRASQSVRSFLAWYQQKPGQAPRLLIYD

ASNRATGIPARFSGSGSGTDFTLTISSLEPEDFAVYYCQQRSNWPPTFGQ

GTKVEIK.

In another aspect, the antibodies of the present invention comprise a HCVR amino acid sequence:

(SEQ ID NO: 25)
QLQVQESGPGLVKPSETLSLTCTVSGGSISNSYFSWGWIRQPPGKGLEWI

GSFYYGEKTYYNPSLKSRATISIDTSKSQFSLKLSSVTAADTAVYYCPRG

PTMIRGVIDSWGQGTLVTVSS
and a LCVR amino acid sequence:

(SEQ ID NO: 27)
EIVLTQSPATLSLSPGERATLSCRASQSVRSYLAWYQQKPGQAPRLLIYD

ASNRATGIPARFSGSGSGTDFTLTISSLEPEDFAVYYCQQRSNWPPTFGQ

GTKVEIK.

In another aspect, the antibodies of the present invention comprise:
i) a heavy chain of SEQ ID NO: 37 and a light chain of SEQ ID NO: 4; or
ii) a heavy chain of SEQ ID NO: 6 and a light chain of SEQ ID NO: 14.

In another aspect, the antibodies of the present invention comprise two heavy chains of SEQ ID NO: 37 and two light chains of SEQ ID NO: 4.

In another aspect, the present invention comprises a human TGFβRII-binding fragment.

It is contemplated that any of the antibodies of the present invention may be administered to a subject in need thereof. Accordingly, one aspect of the invention provides a pharmaceutical composition comprising an antibody or fragment of the present invention and a pharmaceutically acceptable carrier, diluent or excipient.

In a preferred aspect of the invention, the antibody or a functional fragment thereof competes for binding to the extracellular domain of TGFβRII in a competition ELISA assay with a competing antibody, wherein said competing antibody binds TGFβRII with a $K_D$ of less than 100 pM at room temperature (20-25° C.).

In another preferred aspect of the invention, the antibody of the invention blocks binding of human TGFβ1, TGFβ2, or TGFβ3 to human TGFβRII with an $IC_{50}$ of less than 1.0 nM as determined by ELISA.

It is also contemplated that the mAbs of the present invention may be used for treating fibrosis or fibrotic diseases of the lungs, liver, and kidneys. In one aspect, a method is provided for treating fibrosis or fibrotic diseases of the lungs, liver, and kidneys comprising administering to a subject in need of such treatment an effective amount of a mAb of the present invention.

One aspect of the present invention provides the antibodies of the present invention for use as a medicament. One aspect of the present invention provides the antibodies of the present invention for use in the treatment of cancer. A further aspect of the invention provides antibodies for use in the treatment of breast, lung or pancreatic cancer. The antibodies of the invention may be used in the treatment of cancer together with an anti-cancer agent. Another aspect of the present invention provides a product containing the antibody or fragment and an additional anti-cancer agent for treatment in combination for simultaneous, separate or sequential use in therapy.

A preferred aspect of the invention provides an isolated antibody that specifically binds the extracellular domain of hTGFβRII, comprising a CDRH1 having the sequence GGSISX$_1$SX$_2$X$_3$ (SEQ ID NO: 17), wherein X$_1$ is N or S, X$_2$ is Y or S, and X$_3$ is F or Y; a CDRH2 having the sequence SFYYX$_1$X$_2$X$_3$TYYX$_4$PSLKS (SEQ ID NO: 18), wherein X$_1$ is G or S, X$_2$ is E or G, X$_3$ is K or I, X$_4$ is N or S; a CDRH3 having the sequence GX$_1$TMIRGX$_2$X$_3$DX$_4$ (SEQ ID NO: 42), wherein X$_1$ is P or F, X$_2$ is V or A, X$_3$ is I or L, X$_4$ is S or Y; a CDRL1 having the sequence RASQSVRSX$_1$LA (SEQ ID NO: 20), wherein X$_1$ is Y, or F; a CDRL2 having the sequence DASNRAT (SEQ ID NO: 11); and a CDRL3 having the sequence QQRSNWPPT(SEQ ID NO:12).

Another aspect of the present invention provides a method of treating cancer in a patient comprising administering to the patient an effective amount of the antibodies of the invention. The cancer may be breast, lung or pancreatic cancer. The antibodies may be administered to the patient, with an effective amount or another anti-cancer agent, simultaneously, separately or sequentially. The anti-cancer agent may be cyclophosphamide.

Another aspect of the invention provides an isolated antibody that specifically binds to the extracellular domain of human TGFβ receptor II (TGFβRII) comprising: a CDRH1 having the sequence GGSISNSYF (SEQ ID NO: 1), a CDRH2 having the sequence SFYYGEKTYYNPSLKS (SEQ ID NO: 2), a CDRH3 having the sequence GPTMIRGVIDS (SEQ ID NO: 3), a CDRL1 having the sequence RASQSVRSYLA (SEQ ID NO: 10), a CDRL2 having the sequence DASNRAT (SEQ ID NO: 11), and a CDRL3 having the sequence QQRSNWPPT (SEQ ID NO: 12); or a CDRH1 having the sequence GGSISSSSY (SEQ ID NO: 7), a CDRH2 having the sequence SFYYSGITYYSPSLKS (SEQ ID NO: 8), a CDRH3 having the sequence GFTMIRGALDY (SEQ ID NO: 9), a CDRL1 having the sequence RASQSVRSFLA (SEQ ID NO: 16), a CDRL2 having the sequence DASNRAT (SEQ ID NO: 11), and a CDRL3 having the sequence QQRSNWPPT (SEQ ID NO: 12), or a TGFβRII-binding fragment of the antibody.

Another aspect of the invention comprises an antibody of the invention, comprises a HCVR amino acid sequence:

(SEQ ID NO: 25)
QLQVQESGPGLVKPSETLSLTCTVSGGSISNSYFSWGWIRQPPGKGLEWI

GSFYYGEKTYYNPSLKSRATISIDTSKSQFSLKLSSVTAADTAVYYCPRG

PTMIRGVIDSWGQGTLVTVSS and a LCVR amino acid sequence:

(SEQ ID NO: 27)
EIVLTQSPATLSLSPGERATLSCRASQSVRSYLAWYQQKPGQAPRLLIYD

ASNRATGIPARFSGSGSGTDFTLTISSLEPEDFAVYYCQQRSNWPPTFGQ

GTKVEIK;

or a HCVR amino acid sequence:

(SEQ ID NO: 33)
QLQLQESGPGLVKPSETLSLTCTVSGGSISSSSYSWGWIRQPPGKGLEWI

GSFYYSGITYYSPSLKSRIIISEDTSKNQFSLKLSSVTAADTAVYYCASG

FTMIRGALDYWGQGTLVTVSS, and a LCVR amino acid sequence:

(SEQ ID NO: 35)
EIVLTQSPATLSLSPGERATLSCRASQSVRSFLAWYQQKPGQAPRILIYD

ASNRATGIPARFSGSGSGTDFTLTISSLEPEDFAVYYCQQRSNWPPTFGQ

GTKVEIK, or a TGFβRII-binding fragment of the antibody.

Another aspect of the invention comprises an antibody of the invention comprising a heavy chain of SEQ ID NO: 37 and a light chain of SEQ ID NO: 4; or a heavy chain of SEQ ID NO: 6 and a light chain of SEQ ID NO: 14.

An "isolated antibody" is an antibody that (1) has been partially, substantially, or fully purified from a mixture of components; (2) has been identified and separated and/or recovered from a component of its natural environment; (3) is monoclonal; (4) is free of other proteins from the same species; (5) is expressed by a cell from a different species; or (6) does not occur in nature. Contaminant components of its natural environment are materials which would interfere with diagnostic or therapeutic uses for the antibody, and may include enzymes, hormones, and other proteinaceous or non-proteinaceous solutes. Examples of isolated antibodies include an antibody that has been affinity purified, an antibody that has been made by a hybridoma or other cell line in vitro, and a human antibody derived from a transgenic mouse.

As used herein, the term "antibody" refers to immunoglobulin molecules comprising 4 polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region contains three domains, CH1, CH2 and CH3. Each light chain is comprised of a light chain variable region (abbreviated herein as LCVR or VL) and a light chain constant region. The light chains of antibodies (immunoglobulins) from any vertebrate species can be assigned to one of two clearly distinct types, called kappa (K) and lambda (λ), based on the amino acid sequences of their constant domains. The variable regions of kappa light chains are referred to herein as VK. The expression VL, as used herein, is intended to include both the variable regions from kappa-type light chains (VK) and from lambda-type light chains. The light chain constant region is comprised of one domain, CL. The VH and VL regions include regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1-CDR1-FR2-CDR2-FR3-CDR3-FR4.

"CDRH1" refers to the first CDR region in an antibody heavy chain, "CDRH2" refers to the second CDR region in an antibody heavy chain, and "CDRH3" refers to the third CDR region in an antibody heavy chain. "CDRL1" refers to the first CDR region in an antibody light chain, "CDRL2" refers to the second CDR region in an antibody light chain, and "CDRL3" refers to the third CDR region in an antibody light chain.

The term "antigen-binding fragment" refers to a portion or fragment of an intact antibody, comprising the antigen-binding or variable region thereof. Examples of antibody fragments include less than full length antibodies, e.g., a Fab fragment, F(ab')$_2$, or a single-chain variable fragment (scFv). Likewise encompassed by the invention are diabodies, linear antibodies, single-chain antibodies, fusion proteins, recombinant proteins, and multivalent or multispecific antibodies formed or partly formed from an antigen-binding fragment of the present invention.

The term "TGF-beta receptor II" or "TGFβRII" as used herein refers to a cell surface receptor that binds a ligand, including, but not limited to, TGFβ1, TGFβ2, and TGFβ3, and as a result initiates a signal transduction pathway within the cell. Human TGFβRII is a transmembrane protein that is encoded by the DNA sequence of SEQ ID NO: 40.

The antibodies of the present invention bind human TGFβRII, more specifically the extracellular domain of human TGFβRII, and block binding of human TGFβ1, TGFβ2, and TGFβ3 to human TGFβRII.

The antibodies of the present invention also include those for which binding characteristics have been improved by direct mutation, methods of affinity maturation, phage display, or chain shuffling by methods known in the art. The antibodies of the invention include any combination of heavy and light chains (either full length or portions thereof) from the antibodies of the invention, referred to as TGF1 and TGF3.

The antibodies of the present invention can be used as a template or parent antibody to make additional antibodies of the invention using a variety of techniques including CDR-grafting, veneering or resurfacing, and chain shuffling (e.g., as disclosed in U.S. Pat. No. 5,565,332). The human antibodies of the invention may include amino acid residues not encoded by human germline immunoglobulin sequences (e.g., mutations introduced by random or site-specific mutagenesis in vitro or by somatic mutation in vivo), for example in the CDRs. The human antibody can have at least one position replaced with an amino acid residue, e.g., an activity enhancing amino acid residue which is not encoded by the human germline immunoglobulin sequence, and in so doing generate further variable region amino acid sequences derived from the sequences herein provided.

In one approach the parent antibody CDRs are grafted into a human framework that has high sequence identity with the parent antibody framework. The sequence identity of the new framework will generally be at least 80%, at least 85%, or at least 90% with the corresponding framework in the parent antibody. This grafting may result in reduction in binding affinity compared to the parent antibody. If so, the framework can be back-mutated to the parent framework at certain positions based on specific criteria published by Queen (Queen, et al., Proc. Natl. Acad. Sci. USA 88, 2869 (1991)). Further methods that may be used include, for example, Jones et al., Nature, 321:522 (1986); Riechmann et al., Nature, 332:323-327 (1988); and Verhoeyen et al., Science, 239:1534 (1988).

Up to all 20 alternative naturally occurring amino acids may be introduced at a specific substitution site. The in vitro selection process defined here may then be suitably used to screen these additional variable region amino acid sequences for Fab fragments having the claimed cross reactivity and in vitro. In this way further Fab fragments are identified that are suitable for preparing a humanized antibody in accordance with the present invention. Preferably the amino acid substitution within the frameworks is restricted to one, two or three positions within one or each of the framework sequences disclosed herein. Preferably amino acid substitution within the CDRs is restricted to one to three positions within one or each CDR, more preferably substitution at one or two amino acid positions within one or each CDR is performed. Further preferred, amino acid substitution is performed at one or two amino acid positions in the CDRs of the heavy chain variable region. A suitable methodology for combining CDR and framework substitutions to prepare alternative antibodies according to the present invention, using an antibody described herein as a parent antibody, is provided in Wu et al., J. Mol. Biol., 294:151-162.

The term "$K_D$" refers to the dissociation constant of a particular antibody-antigen interaction. It is calculated by the formula: $k_{off}/k_{on}=K_D$. The term "$k_{on}$" refers to the association or on rate constant, or specific reaction rate, of the forward, or complex-forming, reaction, measured in units: $M^{-1}sec^{-1}$. The term "$k_{off}$" refers to the dissociation or off rate constant, or specific reaction rate, for dissociation of an antibody from the antibody/antigen complex, measured in units: 1/second. The binding affinity of an antibody of the present invention is often correlated with a lower $k_{off}$ more so than a higher $k_{on}$, however, not being bound by theory, both improved $k_{off}$ and $k_{on}$, embodiments are encompassed. In a more preferred aspect, antibodies of the present invention are high potency antibodies, or fragments thereof, generally exhibiting low $k_{off}$ values.

In certain aspects, the antibodies of the present invention have a $K_D$ of about 1 pM to about 200 pM, about 5 pM to about 100 pM or about 10 pM to about 80 pM.

As used herein, the terms "blocks binding" and "inhibits binding," used interchangeably, refer to blocking/inhibition of binding of a cytokine to its receptor, resulting in complete or partial inhibition or reduction of a biological function of the cytokine/receptor signal pathway. Blocking/inhibition of binding of TGFβ to TGFβRII is assessed by measuring the complete or partial inhibition or reduction of one or more in vitro or in vivo indicators of TGFβ activity such as, receptor binding, an inhibitory effect on cell growth, chemotaxis, apoptosis, intracellular protein phosphorylation, or signal transduction. The ability to block the binding TGFβ to TGFβRII may be measured by ELISA as described herein. The ability to inhibit TGF3 activity may be assessed by measuring the inhibition of Smad2 phosphorylation in a cell, for example, in human MDA-MB-231 cells as described herein.

The antibodies of the present invention block binding of human TGF131, TGFβ2, or TGFβ3 to human TGFβRII with an $IC_{50}$ of about 0.05 nM to about 1.0 nM, about 0.08 nM to about 0.75 nM, or about 0.10 nM to about 0.60 nM.

The antibodies of the present invention inhibit TGFβ-induced Smad2 phosphorylation with an $IC_{50}$ of less than or equal to about 2.0 nM to about 30 nM, about 3.0 nM to about 15.0 nM or about 4.0 nM to about 7.5 nM in an in vitro blocking assay, for example, in an in vitro MDA-MB-231 cell blocking assay as described herein.

Antibodies may have a glycosylation pattern that is different or altered from that found in the native species. As is known in the art, glycosylation patterns may depend on the sequence of an antibody (e.g., the presence or absence of particular glycosylation amino acid residues), or the host cell, or the organism in which the protein is produced. It is contemplated that the antibodies of the present invention include the antibodies disclosed herein as well as glycosylation variants thereof.

The present invention also includes expression vectors comprising any of the polynucleotides described herein. Exemplary vectors include plasmids, phagemids, cosmids, viruses and phage nucleic acids or other nucleic acid molecules that are capable of replication in a prokaryotic or eukaryotic host such as a cell, e.g., a mammalian cell. The vector may be an expression vector, wherein the polynucleotide encoding the antibody is operably linked to expression control elements. Typical expression vectors contain transcription and translation terminators, initiation sequences, and promoters useful for regulation of the expression of the nucleic acid molecules of the invention. The vectors may also contain genetic expression cassettes containing an independent terminator sequence, sequences permitting replication of the vector in both eukaryotes and prokaryotes, i.e., shuttle vectors and selection markers for both prokaryotic and eukaryotic systems. The vectors typically contain a marker to provide a phenotypic trait for selection of transformed hosts such as conferring resistance to antibiotics such as ampicillin or neomycin.

Suitable promoters include constitutive promoters and inducible promoters. Representative promoters include promoters derived from the human cytomegalovirus, metallothionein promoter, SV-40 early promoter, SV-40 later promoter, murine mammary tumor virus promoter, Rous sarcoma virus promoter and polyhedrin promoter.

The invention also includes recombinant cells containing a nucleic acid molecule or an expression vector of the invention. "Recombinant cell" means a non-human multicellular organism or a "host cell," which refers to a cell or population of cells into which a nucleic acid molecule or vector of the invention is introduced. A host cell of the present invention may be a eukaryotic cell or cell line, such as a plant, animal, vertebrate, mammalian, rodent, mouse, primate, or human cell, or cell line.

In one aspect, a host of the present invention may be prokaryotic or eukaryotic. Suitable prokaryotic hosts include, for example, *Escherichia coli*, such as *E. coli* SG-936, *E. coli* HB 101, *E. coli* W3110, *E. coli* X1776, *E. coli* X2282, *E. coli* DHI, and *E. coli* MRC1, *Pseudomonas*, *Bacillus*, such as *Bacillus subtilis*, and *Streptomyces*. Suitable eukaryotic cells include yeast and other fungi, insect cells, plant cells, human cells, and animal cells, including mammalian cells, such as hybridoma lines, COS cells, NS0 cells and CHO cells.

The invention includes methods of producing an antibody by culturing a recombinant cell expressing one or more nucleic acid sequences encoding an antibody of the present invention, and recovering the antibody from the culture medium. An antibody so expressed is typically purified or isolated after expression. Antibodies may be isolated or purified in a variety of ways known to those skilled in the art. Standard purification methods include chromatographic techniques, electrophoretic, immunological, precipitation, dialysis, filtration, concentration, and chromatofocusing techniques. As is well known in the art, a variety of natural proteins bind antibodies, for example bacterial proteins A, G, and L, and these proteins may find use in the present invention for purification. Purification can often be enabled by a particular fusion partner. For example, proteins may be purified using glutathione resin if a GST fusion is employed, $Ni^{+2}$ affinity chromatography if a His-Tag is employed or immobilized anti-Flag antibody if a His-Tag is used. The antibody can be purified by separating it from the culture medium. Antibodies comprising more than one chain can be produced by expressing each chain together in the same host; or as separate chains, which are assembled before or after recovery from the culture medium.

Antibodies may be screened using a variety of methods, including, but not limited to, in vitro assays, in vitro cell-based assays, in vivo assays, and selection technologies. Properties of antibodies that may be screened include, but are not limited to, biological activity, stability, solubility, and binding affinity for the target. Multiple properties may be screened simultaneously or individually. Proteins may be purified or unpurified, depending on the requirements of the assay. In one aspect, the screen is a qualitative or quantitative binding assay for binding of antibodies to a protein or non-protein molecule that is known or thought to bind the antibody. In one aspect, the screen is a binding assay for measuring binding to the target antigen. Automation and high-throughput screening technologies may be utilized in the screening procedures. Screening may employ the use of a fusion protein or labeled-protein. Binding assays can be carried out using a variety of methods known in the art, including, but not limited to, ELISA. As used herein, "competes for binding" refers to the situation in which an antibody reduces binding or signaling by at least about 20%, 30%, 50%, 70% or 90% as measured by a technique available in the art, e.g., competition ELISA or Kd measurement with BIAcore, but is not intended to completely eliminate binding.

One apparatus well known in the art for measuring binding interactions is a BIAcore™ 2000 instrument which is commercially available through Pharmacia Biosensor (Uppsala, Sweden).

This invention includes a pharmaceutical composition comprising an antibody of the invention described herein and a pharmaceutically acceptable carrier, diluent, or excipient. The pharmaceutical composition can optionally contain other therapeutic ingredients. As used herein, "pharmaceutically acceptable carrier" includes solvents, dispersion media, coatings, antibacterial and antifungal agents, isotonic and absorption delaying agents and the like that are physiologically compatible.

Examples of pharmaceutically acceptable carriers include water, saline, phosphate buffered saline, dextrose, glycerol, ethanol and the like, as well as combinations thereof. Pharmaceutically acceptable carriers may further include minor amounts of auxiliary substances such as wetting or emulsifying agents, preservatives or buffers, which enhance the shelf life or effectiveness of the antibody, as well as isotonic agents such as sugars, polyalcohols such as mannitol and sorbitol, and sodium chloride.

The pharmaceutical compositions of the present invention may be formulated in a variety of ways, including, for example, liquid, semi-solid and solid dosage forms, such as liquid solutions (e.g., injectable and infusible solutions), dispersions or suspensions, powders, liposomes and suppositories. The compositions are preferably in the form of injectable or infusible solutions.

The preferred mode of administration is parenteral (e.g., intravenous, subcutaneous, intraperitoneal, intramuscular). Particularly preferred modes are intravenous infusion or injection, intramuscular injection and subcutaneous injection. Said compositions are designed in accordance with conventional techniques as in e.g., Remington, *The Science and Practice of Pharmacy,* 19th Edition, Gennaro, Ed., Mack Publishing Co., Easton, Pa. 1995 which provides a compendium of formulation techniques as are generally known to practitioners.

Effective doses of the compositions of the present invention for treatment of a disease or disorder as described herein vary depending upon many different factors, including means of administration, target site, physiological state of the subject, whether the subject is human or an animal, other medications administered, and whether treatment is prophylactic or therapeutic. Treatment dosages may be titrated using routine methods known to those of skill in the art to optimize safety and efficacy.

The terms "treat," "treating," and "treatment" refer to therapeutic treatment, wherein the object is to slow down (lessen) an undesired physiological change associated with a disease or disorder. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, and remission (whether partial or total) of the disease or disorder, whether detectable or undetectable. "Treatment" can also mean prolonging survival as compared to expected survival if not receiving treatment. Those in need of treatment include those already with the disease or disorder as well as those prone to having the disease or disorder.

The pharmaceutical compositions of the present invention may include a "therapeutically effective amount" of an anti-TGFβRII antibody of the present invention. A "therapeutically effective amount" means an amount effective at dosages and for periods of time necessary to achieve the desired therapeutic result. A therapeutically effective amount of the antibody may vary according to factors such as the disease state, age, sex, weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form means a dose containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically effective amount of an antibody of the invention is 0.1-50 mg/kg. In another aspect the effective amount of an antibody is 3-35 mg/kg. In another aspect, the effective amount is 10-25 mg/kg. In another aspect, the effective amount is 5-20 mg/kg. In another aspect, the effective amount is 3-15 mg/kg. In another aspect, the effective amount is 2-10 mg/kg. In another aspect, the effective amount is 5-10 mg/kg. In another aspect the effective amount of an antibody is 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The antibodies of the present invention can be used for treating cancer. Cancer is considered to be a large group of diseases classified by the tissue of origin and the degree of tumor progression. Cancer can also be classified as primary tumors and metastatic tumors, as well as refractory or recurrent tumors. Refractory tumors are tumors that fail to respond or are resistant to treatment with chemotherapeutic agents alone, antibodies alone, radiation alone or combinations thereof. Recurrent tumors are tumors that appear to be inhibited by treatment with such agents, but recur up to five years, sometimes up to ten years or longer after treatment is discontinued.

Cancer that may be treated also includes tumors that are not vascularized, or not yet substantially vascularized, as well as vascularized tumors. Cancer may be comprised of non-solid tumors or solid tumors.

Anti-TGFβRII antibodies of the invention can also be used to treat TGFβRII-related disorders, diseases, or conditions that include chronic and acute disorders or diseases, including those pathological conditions that predispose the mammal to the disorder. Disorders to be treated herein include fibrosis caused by an arterial injury, an infection, rheumatoid arthritis, diabetes or a diabetic condition, or a malignancy, diseases characterized by accumulation of extracellular matrix, diseases caused by TGFβRII signaling, conditions caused by suppression of the immune system due to TGFβRII mediated activity, acute immune deficiencies resulting from severe injuries, burns, and illnesses such as viral or bacterial infections, and multi-organ systemic illnesses due to TGFβRII-mediated activity.

TGFβs play a significant role in self-renewal, proliferation and differentiation of hematopoietic stem cells. The antibodies of the present invention may be used for the enrichment and regeneration of stem cells, and facilitating of stem cell-based therapeutics in post-myocardial infarction, neuronal disorders and various types of tissue regeneration.

The antibodies of the present invention may be administered alone, or in combination with an anti-neoplastic agent other than anti-human TGFβRII antibodies, including chemotherapeutic agents, radiation, other TGFβRII antagonists, TGFβ antagonists, anti-angiogenesis agents, antibodies to other targets, and small molecules. Anti-TGFβRII antibodies are especially useful in treating anti-VEGF-A resistant tumors. The administration of the antibodies with other antibodies and/or treatments may occur simultaneously, or separately, via the same or different route, at the same or different times.

The methods of treatment described herein can be used to treat any suitable mammal, including primates, such as monkeys and humans, horses, cows, cats, dogs, rabbits, and rodents such as rats and mice.

The following examples are offered for illustrative purposes only, and are not intended to limit the scope of the present invention in any way.

EXAMPLES

Materials and Cell Lines

Human TGFβ1, TGFβ2, and TGFβ3 may be produced recombinantly and purified or may be purchased, for example from R&D Systems. Recombinant TGFβRII Fc fusion proteins (TGFβRII-Fc) and soluble recombinant TGFβRII alkaline phosphatase (TGFβRII-AP) proteins may be expressed in stably-transfected cells and purified from cell culture supernatants following the procedures known to one skilled in the art (Tessler, *J. Biol. Chem.*, 269:12456-12461 (1994)).

The human cancer cell lines BXPC-3, PANC-1, MDA-MB-231 and mouse tumor cell lines EMT6, 4T1, CT26, B16-F10 and myeloma cell lines P3-X63-Ag8.653 may be obtained from the American Type Tissue Culture Collection (Manassas, Va.). MDA-MB-231 luciferase transfectant cell line may be obtained from Sunnybrook Health Sciences Centre. Cells may be maintained in RPMI1640 or IMDM medium (Invitrogen/Life Technologies, Inc., Rockville, Md.) containing 10% fetal calf serum (FCS, Hyclone, Logan, Utah). All cells may be maintained at 37° C. in a humidified, 5% $CO_2$ atmosphere.

Generation of Anti-TGFβRII mAbs

Anti-TGFβRII mAbs may be generated essentially by standard hybridoma technology (Harlow & Lane, ed., *Antibodies: A Laboratory Manual*, Cold Spring Harbor, pages 211-213 (1998)) using human immunoglobulin transgenic mice (Medarex, San Jose, Calif.), which produce human immunoglobulin gamma heavy and kappa light chains, or Lewis rats (Charles River Laboratories, Wilmington, Mass.). Briefly, mice or rats are immunized subcutaneously (s.c.) with recombinant human or mouse TGFβRII-Fc protein emulsified with complete Freund's adjuvant. Animals are intraperitoneally (i.p.) boosted three times with the same TGFβRII-Fc protein in incomplete Freund's adjuvant. The animals are rested for a month before they receive a final i.p. boost of 50 micrograms (μg) of TGFβRII-Fc protein in phosphate buffer solution (PBS). Splenocytes are harvested from the immunized mice and fused with P3-X63-Ag8.653 plasmacytoma cells using polyethylene glycol (PEG, MW: 1450 KD). After fusion, the cells are resuspended in HAT (hypoxanthine, aminopterin, thymidine) medium supplemented with 10% fetal bovine serum (FBS) and distributed to 96 well plates at a density of 200 microliters per well for establishment of hybridoma cells.

At day 10 to 12 post-fusion, the hybridomas are screened for antibody production and specific binding activity of culture supernatants with TGFβRII protein in ELISA-based binding and blocking assays. Specifically, hybridomas producing anti-TGFβRII mAbs are first identified by detection of TGFβRII-bound antibody with a goat anti-human kappa light chain or anti-mouse IgG horse radish peroxidase (HRP) conjugated antibody according to the following procedure. Human TGFβRII-Fc or mouse TGFβRII-Fc is coated at 100 ng/well on 96 microtiter plates at 4° C. overnight. The coated plates are blocked with the blocking buffer (PBS 0.05% TWEEN® 20 containing 5% dry milk) at room temperature for 2 hours. Hybridoma supernatants or purified antibodies are diluted in PBS with 2% bovine serum albumin (BSA) and 0.05% TWEEN® 20 (ELISA buffer) and incubated in TGFβRII-coated, 96-well, microtiter plates for 30 minutes. Plates are washed with the ELISA buffer and incubated with goat anti-human kappa light chain or anti-mouse IgG-HRP conjugate for 30 minutes. TMB (3,3', 5,5'-tetra-methylbenzidine) substrate is used for color development following the manufacturer's instructions. The absorbance at 450 nanometers (nm) is read for quantification of binding activity of antibodies. For identification of hybridomas producing neutralizing anti-TGFβRII mAbs, an ELISA based blocking assay is performed according to the following procedure. TGFβ1, TGFβ2, or TGFβ3 is coated at 200 ng per well on 96-well plates, and wells are then blocked with the blocking buffer. Hybridoma supernatants are incubated with ELISA buffer containing TGFβRII-AP in TGFβ-coated, 96-well microtiter plates for 1 hour. After washing, p-nitrophenyl phosphate (PNPP) substrate for AP is added to the wells for color development following the manufacturer's instructions. The absorbance at 405 nm is read for quantification of TGFβRII-binding to TGFβ1, TGFβ2, and TGFβ3. Optical density (OD) values are read on a microtiter plate reader (Molecular Devices Corp., Sunnyvale, Calif.).

The positive hybridomas are subcloned three times by a limiting dilution culture for establishment of monoclonal hybridoma cell lines.

Table 1 shows the amino acid sequences of the light chain and heavy chain CDRs of mAbs TGF1 and TGFβ.

TABLE 1

Amino acid sequences of the light chain and heavy chain CDRs of anti-human TGFβRII mAbs

|  | mAb TGF1 | mAb TGF3 |
|---|---|---|
| CDRH1 | GGSISNSYF (SEQ ID NO: 1) | GGSISSSSY (SEQ ID NO: 7) |
| CDRH2 | SFYYGEKTYYNPSLKS (SEQ ID NO: 2) | SFYYSGITYYSPSLKS (SEQ ID NO: 8) |

TABLE 1-continued

Amino acid sequences of the light chain and heavy chain CDRs of anti-human TGFβRII mAbs

|  | mAb TGF1 | mAb TGF3 |
|---|---|---|
| CDRH3 | GPTMIRGVIDS (SEQ ID NO: 3) | GFTMIRGALDY (SEQ ID NO: 9) |
| CDRL1 | RASQSVRSYLA (SEQ ID NO: 10) | RASQSVRSFLA (SEQ ID NO: 16) |
| CDRL2 | DASNRAT (SEQ ID NO: 11) | DASNRAT (SEQ ID NO: 11) |
| CDRL3 | QQRSNWPPT (SEQ ID NO: 12) | QQRSNWPPT (SEQ ID NO: 12) |

The SEQ ID NOs of the amino acid sequences and the DNA sequences encoding the amino acid sequences of HCVRs, LCVRs, the heavy chains (HCs), and the light chains (LCs) for mAbs TGF1 and TGF3 are provided in Table 2 below.

TABLE 2

SEQ ID NOs of the amino acid sequences and the encoding DNA sequences of anti-human TGFβRII mAbs

|  | mAb TGF1 | mAb TGF3 |
|---|---|---|
| Amino acid Sequences | | |
| HCVR | (SEQ ID NO: 25) | (SEQ ID NO: 33) |
| LCVR | (SEQ ID NO: 27) | (SEQ ID NO: 35) |
| HC | (SEQ ID NO: 37) | (SEQ ID NO: 45) |
|  | (SEQ ID NO: 55)* | (SEQ ID NO: 59)* |
| LC | (SEQ ID NO: 39) | (SEQ ID NO: 47) |
|  | (SEQ ID NO: 56)* | (SEQ ID NO: 60)* |
| DNA Sequences | | |
| HCVR | (SEQ ID NO: 26) | (SEQ ID NO: 34) |
| LCVR | (SEQ ID NO: 28) | (SEQ ID NO: 36) |
| HC** | (SEQ ID NO: 38) | (SEQ ID NO: 46) |
| LC** | (SEQ ID NO: 40) | (SEQ ID NO: 48) |

*Amino acid sequences with a secretory signal sequence.
**cDNA Sequences include a secretory signal sequence.

Engineering and Expression of Human IgG1 Anti-Human TGFβ Receptor II Antibodies.

The DNA sequences encoding the heavy chain and light chain variable regions of the anti-TGFβRII mAbs may be amplified by PCR for cloning into expression vectors. The heavy chain variable regions may be fused in frame to the human immunoglobulin heavy chain gamma 1 constant region in vector pEE6.1 (Lonza Biologics plc, Slough, Berkshire, UK). The entire human light chain cDNA may be cloned directly into vector pEE12.1 (Lonza Biologics PLC, Slough, Berkshire, UK). Engineered immunoglobulin expression vectors may be stably transfected in NS0 myeloma cells by electroporation and selected in glutamine synthetase selection medium. Stable clones may be screened for antibody expression by anti-human TGFβRII specific binding ELISA. Positive clones may be cultured into serum-free medium culture for antibody production in spinner flasks or bioreactors. Full length IgG1 antibody may be purified by protein an affinity chromatography (Poros A, PerSeptive Biosystems Inc., Foster City, Calif.) and eluted into a neutral buffered saline solution.

The cDNA encoding the heavy chain and light chain variable regions of the anti-human TGFβRII mAbs TGF1 and TGF3 may be cloned and fused in frame to the human immunoglobulin heavy chain gamma 1 constant region in GS (glutamine synthetase) expression vector. Engineered immunoglobulin expression vectors may be stably transfected in CHO cells. Stable clones may be verified for expression of antibody specifically binding to human TGFβRII. Positive clones may be expanded into serum-free medium culture for antibody production in bioreactors. Full length IgG1 antibody may be purified by protein A affinity chromatography and eluted into a neutral buffered saline solution.

Anti-TGFβRII mAbs bind to TGFβRII and block TGFβRII binding to its ligands.

The binding and blocking activity of purified anti-TGFβRII mAbs is determined in ELISA as described in "Generation of anti-TGFβRII mAbs" above. $ED_{50}$ and $IC_{50}$ of the antibodies are analyzed using GraphPad Prism® software 3.03 (GraphPad Software Inc., San Diego, Calif.). Anti-human TGFβRII mAbs TGF1 and TGF3 each separately exhibit binding activity to human TGFβRII with $ED_{50}$s of 0.031-0.059 nM in an ELISA-based binding assay whereas normal human IgG has no binding activity to the receptor. Purified mAbs TGF1 and TGF3 each separately effectively block the binding of human TGFβ1, TGFβ2, or TGFβ3 to human TGFβRII with $IC_{50}$s of 0.10-0.54 nM.

The binding and blocking characteristics of the anti-human TGFβRII antibodies are summarized in Table 3.

TABLE 3

Binding and Blocking Characteristics of anti-human TGFβRII antibodies

| Clone | Binding Activity to Human TGFβRII ($ED_{50}$) by ELISA | Binding Affinity to Human TGFβRII (KD value) by Biacore Analysis | Blocking Activity to Human TGFβRII binding to human TGFβ1, 2, or 3 ($IC_{50}$) by ELISA |
|---|---|---|---|
| TGF1 | 0.059 nM | 0.011 nM | 0.12 nM: TGFβ1<br>0.54 nM: TGFβ2<br>0.19 nM: TGFβ3 |
| TGF3 | 0.031 nM | 0.019 nM | 0.10 nM: TGFβ1<br>0.41 nM: TGFβ2<br>0.13 nM: TGFβ3 |

The binding activity of anti-mouse TGFβRII mAb MT1 to mouse TGFβRII has an $ED_{50}$ of 0.054 nM and the blocking activity of mAb MT1 to mouse TGFβRII binding to mouse TGFβ1, TGFβ2, or TGFβ3 has an $IC_{50}$s value of 0.12-0.54 nM.

The binding and blocking characteristics of mAb MT1 are summarized in Table 4.

TABLE 4

Binding and Blocking Characteristics of anti-mouse TGFβRII mAb MT1

| Binding Activity to Murine TGFβRII ($ED_{50}$) in ELISA | Binding Affinity to Murine TGFβRII ($K_D$ value) Biacore Analysis | Blocking Activity to Murine TGFβRII binding to Murine TGFβ1, 2, or 3 ($IC_{50}$) in ELISA |
|---|---|---|
| 0.054 nM | 0.033 nM | 0.12 nM: TGFβ1<br>0.54 nM: TGFβ2<br>0.19 nM: TGFβ3 |

Binding Affinity of Anti-TGFβRII mAbs.

The binding affinities of anti-TGFβRII mAbs are determined by surface plasmon resonance technology using BIAcore™ 2000 at room temperature (20-25° C.) (Pharmacia, Piscataway, N.J.). Kinetic analyses of the mAbs are performed by immobilization of a fusion protein of recombinant extracellular domain of either mouse TGFβRII (SEQ ID NO: 41), or the extracellular domain of human TGFβRII, which is encoded by (SEQ ID NO: 40) linked, respectively, with either mouse or human Fc or heavy chain constant region, onto a sensor surface at a concentration of from 5 to 100 nM. Anti-human TGFβRII mAbs TGF1 and TGF3 exhibit a high affinity, with $K_D$ values of 11, 78, 19 pM, respectively. Anti-murine TGFβRII mAb MT1 exhibits a high affinity, with a $K_D$ value of 33 pM.

The kinetics of the mAbs are summarized in Table 5.

TABLE 5

Kinetics of Anti-human TGFβRII mAbs

| mAb | $K_{on}$ (1/Ms) | $K_{off}$ (1/s) | $K_D$ (M) |
|---|---|---|---|
| TGF1 | $1.5 \times 10^6$ | $1.7 \times 10^{-5}$ | $1.1 \times 10^{-11}$ |
| TGF3 | $1.4 \times 10^6$ | $2.7 \times 10^{-5}$ | $1.9 \times 10^{-11}$ |

Species Specificity of Anti-Human TGFβRII mAbs.

The specificity of anti-human TGFβRII mAbs is determined by measuring the reactivity of the antibodies to human TGFβRII or mouse TGFβRII by ELISA. Anti-human TGFβRII mAb TGF1 exhibits no cross-reactivity with mouse TGFβRII, whereas mAb TGF3 exhibits intermediate or minimal cross reactivity with mouse TGFβRII. However, mAb TGF3 does not block human TGFβ1 binding to mouse TGFβRII.

Binding of Anti-TGFβRII mAbs to Native TGFβRII on TGFβRII Expressing Cells.

Binding activity of anti-human TGFβRII mAb TGF1 and fluorescein isothiocyanate (FITC)-labeled goat anti-human IgG antibody may be determined by a staining assay with 293-human TGFβRII transfectant cells and human carcinoma cells. Specifically, aliquots of transfectant cells, carcinoma cells, spleen cells, or lymph node cells are harvested from subconfluent cultures and incubated with fluorescein-labeled or unlabeled primary antibodies to desired molecules in PBS with 1% BSA (staining buffer) for 1 hour on ice. A matched IgG isotype is used as a negative control. Cells are washed twice with the staining buffer and then incubated with FITC, Phycoerythrin (PE) or Alxas Red labeled species-specific secondary antibody to primary antibody (BioSource International, Camarillo, Calif.) in the buffer for 30 min on ice. Cells are washed as above and analyzed on a flow cytometer. Dead cells and debris are eliminated from the analysis on the basis of forward and sideways light scatter. The mean fluorescent intensity units (MFIU) are calculated as the mean log fluorescence multiplied by the percentage of positive population. The mean fluorescent intensity ratio (MFIR) is calculated to quantitate relative expression levels of TGFβRII in the cell lines. The MFIR is the mean fluorescence intensity (MFI) of cells stained with TGFβRII specific mAb divided by the MFI of cells stained with an isotype control antibody.

Anti-human TGFβRII mAb TGF1 demonstrates binding reactivity with the 293-human TGFβRII transfectant cells and MDA-MB-231 human breast carcinoma cells with MFIRs of 46 and 209, respectively whereas normal human IgG has no reactive with the cells. The results indicate that mAb TGF1 has specific reactivity with native human TGFβRII expressed on the cell surface.

Inhibitory Activity of Anti-TGFβRII Mabs on Activation of TGFβRII Downstream Kinase Smad2 in Response to TGFβ1.

Phosphorylation of Smad2 (p-Smad2) induced by TGFβ is a typical downstream signaling pathway of TGFβ signaling through TGFβRII that mediates cellular biological responses such as proliferation, motility, survival, and differentiation in variety of cell types. The ability of anti-human TGFβRII and anti-human mouse TGFβRII mAbs to inhibit p-Smad2 activation may be determined by using 4T1 murine breast cancer cells and MDA-MB-231 human breast carcinoma cells according to the following procedure. Briefly, cells are grown to 80% confluence in FCS-containing medium. After replacing the culture medium with serum free medium, cells are treated with antibody or isotype control in the presence of 10 ng/mL TGF3 for 1 hour. After washing, cell lysates are prepared with lysis buffer and subjected to electrophoresis and Electro-Transfer to nitrocellulose membrane. Phosphorylated Smad2 and Smad2 are detected by Western blot using anti-phospho-Smad2 and Smad2 monoclonal antibodies (Millipore Corporate) and electrogenerated chemiluminescence system (ECL), and imaged and quantified by densitometry using a Fuji Image Analyzer.

Anti-TGFβRII mAbs TGF1 and MT1 reduce TGFβ-induced phosphorylation of Smad2 in human MDA-MB-231 and mouse 4T1 breast cancer cells in a dose-dependent manner. The $IC_{50}$s of mAbs TGF1 and MT1 in the p-Smad2 inhibition assays is determined to be 5±0.5 nM, whereas, mAb TGF3 exhibits an $IC_{50}$ lower than 25±0.5 nM.

Inhibitory Activity of Anti-TGFβRII Mabs on In Vitro Migration and Invasion of Tumor Cells.

The inhibitory effect of anti-TGFβRII mAbs on the invasiveness of tumor cells may be determined by in vitro migration and invasion assays. Briefly, carcinoma cells are loaded at a density of $5 \times 10^3$ per well into upper chambers inserted in Collagen I and IV coated lower chambers of 48-well plates in serum-free medium. The cells are treated with mAbs TGF1 or MT1 at doses of 3, 10, and 30 µg/mL in the presence of 10 ng/mL of TGFβ at 37° C. for 24-48 hours. 25 µg/mL TGFβRII-Fc or isotype IgG are used in assays as positive and negative control. The same conditions are used in the invasion assay with the exception that Matrigel-coated upper chambers are used. After incubation, migrated cells in the opposite sides of upper chambers are fixed with 10% buffered neutral formalin, and stained with 2 µg/mL Hoechst 33342, trihydrochloride, trihydrate solution (Invitrogen) and counted at 20× magnification using a Zeiss Digital Image Camera and software Image-Pro Plus 5.1.

Anti-TGFβRII mAbs TGF1 and MT1 significantly inhibited the migration of BXPC-3 human pancreatic carcinoma cells and the invasion of 4T1 murine breast carcinoma cells by 100% (P<0.0001) and 93% (P<0.0005), respectively, when compared to IgG treated control.

These results demonstrate the inhibitory effect of the anti-TGFβRII antibodies of the present invention on invasiveness of cancer cells bearing TGFβRII on their surface.

Inhibitory Activity of Anti-TGFβRII Mabs on VEGF-A Secretion in Tumor Cells.

TGFβs play a role in promoting angiogenesis during progression of pathological conditions through stimulation of VEGF-A secretion in tumor cells and modulation of endothelial cell functions. The inhibitory effect of anti-TGFβRII mAbs on the TGFβ3-induced secretion of VEGF-A in tumor cells may be determined in cell culture.

Briefly, tumor cells are cultured in serum-free medium at 37° C. in an incubator under 5% $CO_2$ in the presence or absence of 10 ng/mL TGFβ and a serial dilution of the mAbs for 48 hours. Alteration of VEGF-A secretion in conditioned culture supernatants is determined using an ELIKON kit (R&D Systems) per manufacturer's instructions.

Anti-human TGFβRII mAb TGF1 at 10 μM/mL inhibits TGFβ-induced production of VEGF-A in MDA-MB-231 human breast tumor cells by 63% (P<0.01). Anti-mouse TGFβRII mAb MT1 at 10 μM/mL inhibits TGFβ-induced production of VEGF-A in 4T1 mouse breast tumor cells 30% (P<0.02).

These results demonstrate that anti-TGFβRII mAbs of the present invention inhibit angiogenesis by reducing TGFβ-induced VEGF-A secretion.

Inhibitory Activity of Anti-TGFβRII Mabs on In Vitro TGFβ-Induced Treg Conversion.

TGF3 has been shown to be capable of inducing naïve T cells to form regulatory T (Treg) cells that have immunosuppressive capacity to negatively control immune response. The inhibitory effect of anti-TGFβRII mAbs on the TGFβ-induced regulatory cell conversion may be evaluated in vitro as follows.

Briefly, purified naïve CD4+ cells are stimulated with 1 μg/mL anti-CD3 antibody and purified antigen presenting cells (APC) in the presence or absence of 10 ng/mL TGF3 and a serial dilution of mAb MT1 in complete RPMI medium at 37° C. in an incubator under 5% $CO_2$ for 7 days. Cells are then harvested for staining of CD25+/Foxp3+Treg cells and stained cells are analyzed on a flow cytometer.

Anti-mouse TGFβRII mAb MT1 at 10 μM/mL reduces the number of TGFβ-induced Treg cells in vitro by 75% (P<0.005) compared to control IgG treated cells.

Inhibitory Activity of Anti-TGFβRII Mabs on Tumor Growth and Metastasis.

The antitumor efficacy of anti-TGFβRII mAbs may be tested in subcutaneous or intravenous metastasis tumor models.

Athymic nude mice (Charles River Laboratories, Wilmington, Mass.), Balb/c mice, or C57B6 mice (Charles River Laboratories, Wilmington, Mass.) may be used for inoculation with mouse or human carcinoma cells. For treatment of established tumors in subcutaneous models, tumors may be allowed to grow to approximately 200 $mm^3$ in size, and then mice may be randomized into groups of 12-15 animals per group. In lung metastasis models, mice may be injected intravenously with tumor cells via tail vein. Animals may receive i.p. administered anti-TGFβRII mAb at a dose of 10-40 mg/kg three times each week. Mice in control groups may receive an equal volume of saline or normal IgG solution. Treatment of animals may be continued for the duration of the experiment. Tumors may be measured twice each week with calipers. Tumor volumes may be calculated using the formula [π/6 (w1×w2×w2)], where "w1" represents the largest tumor diameter and "w2" represents the smallest tumor diameter.

Tumor volume data may be analyzed using repeated-measures ANOVA (RM-ANOVA) to determine the significant differences in tumor sizes among treatments, time points, and treatment-time interactions. Comparisons of in vitro tumor cell growth between treatment and control may be conducted using the two-tailed Student's t test. A P value of less than 0.05 is considered to be statistically significant.

Mice bearing tumors are treated with mAb TGF1 at a dose of 40 mg/kg three times each week 24 hour post intravenous injection of tumor cells or after primary tumors are established. The systemic administration of mAb TGF1 suppresses subcutaneous primary tumor growth of PANC-1 pancreatic carcinoma xenografts (T/C=69%, ANOVA p<0.03), BXPC-3 pancreatic carcinoma xenografts (T/C=30%, ANOVA p<0.0001), and MDA-MB-231 breast carcinoma xenografts (T/C=63%, ANOVA p<0.01).

Anti-mouse TGFβRII mAb MT1 is tested in mouse syngenetic tumor models for determining antitumor activity against primary and metastatic tumors in immunocompetent mice. Mice are injected intravenously (i.v.) with mouse 4T1, CT26 or B16 F10 carcinoma cells or subcutaneously (s.c.) with EMT6 mouse tumor cells. Mice receive administration of mAb MT1 at a dose of 40 mg/kg three times each week 24 hours post i.v. inoculation or after primary subcutaneous tumors are established.

The systemic administration of mAb MT1 significantly suppresses pulmonary metastasis of 4T1, CT26, and B16 F10 tumors by 84% (P<0.0001), 94% (P<0.0001), and 63% P<0.001), respectively. Anti-mouse TGFβRII mAb MT1 inhibits primary tumor growth by 28% (P<0.05) and spontaneous pulmonary metastasis by 84% (P<0.0001) in the EMT6 s.c. tumor model.

Myeloid cells with a Gr-1/CD11b+ phenotype have been reported to play a significant role in promoting metastasis and angiogenesis immunosuppression during tumor progression. CD4/CD25/Foxp3+Treg cells have the ability to suppress the function of Natural Killer cells and cytotoxic T lymphocyte (CTL) immune effector cells against tumor cells. The inhibitory activity of mAb MT1 against immunosuppressive cells, i.e. CD4/CD25/Foxp3/TGFβRII+ Treg cells and Gr-1+/CD11b+/TGFβRII+ myeloid cells is evaluated in an EMT6 s.c. tumor model. The inhibitory effect of anti-TGFβRII antibody on Treg and Gr-1+/CD11b+ myeloid cell population in tumor-bearing mice may be determined by FACS analysis on the alteration of Gr-1+/CD11b+ population and CD4/CD25/Foxp3/TGFβRII+ and Gr-1+/CD11b+/TGFβRII+ population after treatment of mice with mAb MT1.

Anti-mouse TGFβRII mAb MT1 significantly decreases the number of Gr-1+/CD11b+/TGFβRII+ myeloid cells by 95% (P<0.0001) and CD4/CD25/Foxp3/TGFβRII+ Treg cells by 71% (P<0.0005), respectively, in treated mice bearing EMT6 tumors.

These results indicate that anti-TGFβRII antibodies may control the CD4/CD25/Foxp3/TGFβRII+ and Gr-1+/CD11b+ population by inhibition or/and depletion of TGF-βRII+ Treg and myeloid cells.

Fibrosis Model in Mice.

TGFβ is a key regulator in the activation of hepatic stellate cells (HSC) and the differentiation of myofibroblasts, as well as the extracellular matrix accumulation that contributes to fibrosis. Liver fibrosis models in animals have been widely used as experimental models for the evaluation of activity of TGFβ signaling inhibitors to inhibit fibrosis. Collagen deposition is a known indicator of the formation of fibrosis in liver. Therapeutic activity of anti-TGFβRII antibody in protection and intervention of fibrosis may be evaluated in carbon tetrachloride ($CCl_4$) induced liver fibrosis models.

Briefly, C57BL6 mice may be injected i.p. with 1 mL/kg $CCl_4$ solution mixed with corn oil twice a week. Mice in the intervention treatment group may be administered mAb MT1 at doses of 40 mg/kg 3 times each week 14 days after mice are injected i.p. with $CCl_4$. Mice in the control group may be administered a control rat IgG at the same dosing. Eight weeks after $CCl_4$ injection, liver tissues and plasma samples may be collected from treated mice. Plasma levels of alanine aminotransferase (ALT), an indicator of liver dysfunction, may be determined by using a serum ALT kit (Pointe Scientific, Inc. MI). Liver tissues may be evaluated by immunohistochemistry (IHC) analysis with Sirius Red staining of collagen deposition.

In studies conducted essentially as described above, anti-mouse TGFβRII mAb MT1 significantly reduces collagen deposition by 95% (P<00001) in livers of mice given CCl₄ whereas the control rat IgG has no effect. Anti-mouse TGF-βRII mAb MT1 protects liver from dysfunction by 85% (P<0.001) as measured by plasma level of ALT in mice given CCl₄ whereas mice treated with the control rat IgG have significantly higher levels of ALT.

These results suggest that anti-TGFβRII antibody MT1 is efficacious in protecting mice from injury-induced fibrosis and liver dysfunction.

In Vivo Studies on Combination Treatment with mAb MT1 and Cyclophosphamide.

Cyclophosphamide (CTX), a potent cytotoxic agent with the capacity to suppress hematopoietic and myeloid progenitor cells, has been reported to have inhibitory effects on myeloid cells (See, Honeychurch, et al., Cancer Res. 65:7493-7501 (2005)). EMT6-tumor bearing mice may be treated with mAb MT1 alone, CTX alone, or a combination thereof. For instance, Balb/c mice or C57B6 mice (Charles River Laboratories, Wilmington, Mass.) may be used for inoculation with carcinoma cells. Mice with established tumors may be randomized into 12 animals per group, for example. Animals may be i.p. administered 40 mg/kg anti-TGFβRII mAb, 80 mg/kg CXT, or a combination of both 3 times each week. Mice in control groups may receive an equal volume of saline or normal IgG solution. Tumor volumes may be calculated using the formula [π/6 (w1×w2×w2)], where "w1" represents the largest tumor diameter and "w2" represents the smallest tumor diameter.

Combination treatments with anti-mouse TGFβRII mAb MT1 and CTX performed essentially as described above reduces primary tumor growth by 80% (P<0.0001) and spontaneous pulmonary metastasis by 99.99% (P<0.000001) in EMT6 tumor-bearing mice compared to monotherapy with mAb MT1 28% (P<0.05) or CTX 62% (P<0.0005) in inhibition of primary tumor growth and mAb MT1 84% (P<0.0001) or CTX 96% (P<0.00001) in inhibition of metastasis.

The results demonstrate that inhibition of a subset of TGF-βRII-positive myeloid cells by anti-TGFβRII antibody in combination with myeloid cell suppressive chemotherapy is an effective strategy for intervention in tumor growth and metastasis.

I claim:

1. An isolated antibody that specifically binds to the extracellular domain of human TGFβ receptor II (TGFβRII) comprising a CDRH1 having the sequence GGSISNSYF (SEQ ID NO: 1), a CDRH2 having the sequence SFYYGEKTYYNPSLKS (SEQ ID NO: 2), a CDRH3 having the sequence GPTMIRGVIDS (SEQ ID NO: 3), a CDRL1 having the sequence RASQSVRSYLA (SEQ ID NO: 10), a CDRL2 having the sequence DASNRAT (SEQ ID NO: 11), and a CDRL3 having the sequence QQRSNWPPT (SEQ ID NO: 12).

2. The antibody of claim 1, comprising a HCVR amino acid sequence:
QLQVQESGPGLVKPSETLSLTCTVSGG-SISNSYFSWGWIRQPPGKGLEWIGSFYYG EKTYYNPSLKSRATISIDTSKSQFS-LKLSSVTAADTAVYYCPRGPTMIRGVIDSWG QGTLVTVSS (SEQ ID NO: 25) and a LCVR amino acid sequence:
EIVLTQSPATLSLSPGERATLSCRASQS-VRSYLAWYQQKPGQAPRLLIYDASNRAT GIPARFSGSGSGTDFTLTISSLEPED-FAVYYCQQRSNWPPTFGQGTKVEIK (SEQ ID NO: 27).

3. The antibody of claim 1, comprising a heavy chain of SEQ ID NO: 37 and a light chain of SEQ ID NO: 4.

4. The antibody of claim 1 comprising two heavy chains of SEQ ID NO: 37 and two light chains of SEQ ID NO: 4.

5. A pharmaceutical composition comprising the antibody of claim 4 and a pharmaceutically acceptable carrier, diluent, or excipient.

* * * * *